United States Patent [19]
Prause et al.

[11] Patent Number: 6,148,095
[45] Date of Patent: *Nov. 14, 2000

[54] APPARATUS AND METHOD FOR DETERMINING THREE-DIMENSIONAL REPRESENTATIONS OF TORTUOUS VESSELS

[75] Inventors: Guido P. M. Prause, Bremen, Germany; Milan Sonka, Iowa City, Iowa

[73] Assignee: University of Iowa Research Foundation, Iowa City, Iowa

[ * ] Notice: This patent issued on a continued prosecution application filed under 37 CFR 1.53(d), and is subject to the twenty year patent term provisions of 35 U.S.C. 154(a)(2).

[21] Appl. No.: 08/925,489

[22] Filed: Sep. 8, 1997

[51] Int. Cl.$^7$ .............................. G06K 9/00; A61B 8/14
[52] U.S. Cl. .......................... 382/131; 600/467; 128/916
[58] Field of Search ..................................... 382/130, 131, 382/128; 600/463, 437, 467, 466; 128/916

[56] References Cited

U.S. PATENT DOCUMENTS

| | | | |
|---|---|---|---|
| 5,081,993 | 1/1992 | Kitney et al. | 600/466 |
| 5,294,861 | 3/1994 | Nattermann | 310/334 |
| 5,485,840 | 1/1996 | Bauman | 128/660.03 |
| 5,699,805 | 12/1997 | Seward et al. | 600/466 |
| 5,715,825 | 2/1998 | Crowley | 128/602.06 |
| 5,724,978 | 3/1998 | Tenhoff | 128/662.06 |
| 5,771,895 | 6/1998 | Slager | 128/662.06 |
| 5,876,345 | 3/1999 | Eaton et al. | 600/466 |
| 5,902,245 | 3/1999 | Yock | 600/463 |

OTHER PUBLICATIONS

Evans et al. "Accurate Three–Dimensional Reconstruction of Intravascular Ultrasound Data: Spatially Correct Three–Dimensional Reconstructions" Circulation, vol. 93, No. 3, pp. 567–576, Feb. 1, 1996.

Roelandt et al. "Three–Dimensional Reconstruction of Intracoronary Ultrasound Images: Rational, Approaches, Problems, and Directions." Circulation, vol. 90, No. 3, pp. 1044–1055, Aug. 1994.

"Semi–automated segmentation and 3–D reconstruction of coronary trees: Biplane angiography and intravascular ultrasound data fusion", Guido P.M. Prause, Steven C. DeJong, Charles R. McKay and Milan Sonka, SPIE Conf. Medical Imaging, Feb. 11–15, 1996, Newport Beach, CA, SPIE Proceed 2709, 1996, pp. 82–92.

Pellot et al. "An Attempt to 3D Reconstruct Vessel Morphology from X–Ray Projections and Intravascular Ultrasounds Modeling and Fusion." Computerized Medical Imaging and Graphics, vol. 20, No. 3, pp. 141–151, Jun. 1996.

Shekhar et al. "Fusion of Intravascular Ultrasound and Biplane Angiography for Three–Dimensional Reconstruction of Coronary Arteries." Computers in Cardiology, pp. 5–8, Aug. 1996.

Lengyel et al. "Time–Dependent Three–Dimensional Intravascular Ultrasound." Computer Graphics Proceedings, pp. 457–464, 1995.

Laban et al. "ANGUS: a New Approach to Three–Dimensional Reconstruction of Coronary Vessels by Combined use of Angiography and Intravascular Ultrasound." Computers in Cardiology, pp. 325–328, Sep. 1995.

(List continued on next page.)

*Primary Examiner*—Jon Chang
*Attorney, Agent, or Firm*—Fleshner & Kim, LLP

[57] ABSTRACT

Three-dimensional reconstructions of tortuous vessels such as coronary arteries can be obtained by data fusion between biplane angiography and IVUS frames of a pullback sequence. The 3D course of the tortuous vessel is first determined from the angiograms and then combined with the 2D representations regarding the 3D course (e.g., segmented IVUS frames of a pullback sequence) using a data fusion apparatus and method: The determination of the 3D pullback path is represented by the external energy of the tortuous vessel and the internal energy of a line object such as a catheter.

16 Claims, 17 Drawing Sheets

OTHER PUBLICATIONS

Prause et al. "Geometrically Correct 3–D Reconstruction of Coronary Wall and Plaque: Combining Biplane Angiography and Intravascular Ultrasound." Computers in Cardiology, pp. 325–328, Sep. 1996.

Foley et al. "Computer Graphics: Principles and Practice." Addison–Wesley, pp. 478, 488–491, 1996.

Laban, M. et al., "Angus: A New Approach to Three–Dimensional Reconstruction of Coronary Vessels By Combined Use of Angiography and Intravascular Ultrasound", Computers in Cardiology 1995, pp. 325–328.

Lengyel, Jed et al., "Time–Dependent Three–Dimensional Intravascular Ultrasound", Computer Graphics Proceedings, Annual Conference Series, 1995, Aug. 6–11, 1995, pp. 457–464.

Prause, Guido P. M. et al., "Semi–automated segmentation and 3–D reconstruction of coronary trees: Biplane angiography and intravascular ultrasound data fusion", SPIE Conf. Medical Imaging, pp. 82–92, 1996.

Pellot, Clarire et al., "An Attempt to 3D Reconstruct Vessel Morphology From X–Ray Projections and Intravascular Ultrasounds Modeling and Fusion", Cumputerized Medical Imaging and Graphics, vol. 20, No. 3, pp. 141–151, 1996.

Foley, James D. et al. "Computer Graphics, Principles and Practice" 1987 pp. 478–491.

Prause et al. "Accurate 3–D Reconstruction of Tortuous Coronary Vessels Using Biplane Angiography and Intravascular Ultrasound." Proceedings of SPIE, Medical Imaging 1997, pp. 225–234, Feb. 23, 1997.

Klein et al. "3D–Surface Reconstruction of Intravascular Ultrasound Images Using Personal Computer Hardward and a Motorized Catheter Control." Cardiovascular and Interventional Radiology, Springer–Verlag, vol. 15, pp. 97–101, 1992.

APPARATUS AND METHOD FOR DETERMINING THREE-DIMENSIONAL REPRESENTATIONS OF TORTUOUS VESSELS

BACKGROUND OF THE INVENTION

1. Field of the Invention

The present invention is directed to an apparatus and method for three-dimensional reconstructions of tortuous vessels, and in particular, to three-dimensional reconstructions of tortuous vessels such as coronary arteries generated from stacked intravascular ultrasound (IVUS) ECG-gated segmented IVUS frames of a pullback sequence combined by data fusion with biplane angiography.

2. Background of the Related Art

Selective coronary angiography is one related art catheter-based imaging technique used for the diagnosis of coronary artery disease. Coronary contrast angiograms are X-ray projections of the contrast bolus inside the vessel lumen. However, due to the projective nature of angiography, the cross-sectional shape of the lumen remains unknown. Moreover, plaque is visualized only indirectly as reduction of lumen diameter, and vessel wall as well as surrounding tissue (adventitia) are not imaged at all. Disadvantageously, even in two projections, the cross-sectional shape of the stenosis can be only roughly estimated. However, biplane angiography allows for accurate reconstruction of the three-dimensional (3D) course of the vessel centerline.

Another related art imaging technique for qualitative and quantitative assessment of coronary arterial wall and plaque is intravascular ultrasound (IVUS) using a catheter or the like. IVUS offers well-calibrated cross-sectional views of coronary morphology (i.e., lumen, plaque, wall, adventitia). Amount and composition of plaque at local stenosis may be quantitatively analyzed through a catheter pullback and even small amounts of plaque are depicted in diffusely deceased arteries. Disadvantageously, IVUS lacks information regarding the 3D vessel geometry.

In the area of IVUS, an increasing number of today's commercially available imaging systems support the generation of pseudo 3D reconstructions. Possible ECG-gated frames of IVUS pullback sequence are stacked up resulting in a straight vessel reconstruction. Clearly, this method is not able to accurately represent the tortuosity of a coronary artery, and it does not account for the twist and the motion of the catheter during pullback.

The potential of the two techniques to complement each other is based on the information provided in their inherent image characteristics. Further, although IVUS examinations can be preceded, guided and/or followed by coronary contrast angiography, both techniques can acquire images during cardiac catherization. Automated segmentation and quantification methods are available for contrast arteriograms as well as for IVUS images.

To overcome limitations of each imaging technique for accurate 3D reconstruction of tortuous coronary arteries, data fusion between biplane angiography and IVUS pullback imaging is used to derive a spatially correct and clinically useful vessel reconstruction by combining the complementary strengths of both imaging techniques. The 3D course of the pullback path is first derived from biplane angiograms and then fused with the segmented IVUS images of the pullback image sequence. The goal is a 3D vessel reconstruction that is both anatomically complete and geometrically correct so that bendings of the vessel are represented in the reconstruction and plaque is located rotationally correct.

The basic concept of fusion-based 3D reconstructions is illustrated in FIG. 1. The segmented cross sections of an IVUS pullback sequence 100 (left) segmented into lumen, plaque and vessel wall are mapped to the corresponding vessel centerline of the 3D coronary tree vessel segment 110 (right) reconstructed from a biplane contrast angiogram. As discussed in "Semi-automated Segmentation and 3D Reconstruction of Coronary Tree: Biplane Angiography and Intravascular Ultrasound Data Fusion" by G. Prause et al., Proceedings of the Conference on Medical Imaging, Feb. 11–15, 1996 (hereafter Prause et al.) the contents of which are incorporated by reference, the processing steps break down into image acquisition, tree reconstruction, border detection, mapping, and evaluation. Image acquisition includes injecting radiopaque dye into the examined coronary tree and the heart is imaged with a calibrated biplane X-ray system before IVUS pullback. Tree reconstruction includes constructing the 3D centerline of the coronary tree from the geometrically corrected biplane angiograms using an automated segmentation method and manual matching of corresponding branching points. Border detection includes automatically determining the vessel wall and plaque in the acquired IVUS pullback images. During mapping, the IVUS cross-sections are mapped perpendicular to the vessel centerline, the twist of the IVUS catheter is calculated and the vessel reconstruction is rotationally adjusted. Evaluation includes visually and quantitatively analyzing the reconstructed coronary tree and vessel segment.

In the related art techniques, problems arise with data fusion between biplane angiography and IVUS pullback imaging including the definition of the pullback path. Further, several sources of error have been reported that may impede the accuracy of the 3D vessel reconstruction. Most of these errors appear either fully within the IVUS modality or within the angiography modality. These problems include significant processing demands with disjointed 2D IVUS cross-sections and how to position IVUS slices in a vertex area.

In addition to the above, a line object (e.g., an intravascular ultrasound catheter inserted in a coronary vessel) is visualized using two projection images. The goal is to obtain 3D information about the line object (catheter). The related art approach is to independently determine the line object projection in the two projection images and perform their 3D reconstruction according to the calibrated epipolar geometry of the projection acquisition system. Due to projection image ambiguities that are inherent to projection imaging, such an approach may result in reconstructions that are infeasible. For example, ambiguities of the projections if considered independently in individual projections can lead to line object reconstructions having a shape that cannot be physically achieved by the original line object. Thus, the related art apparatus and methods result in 3D reconstructions that cannot happen in actuality (e.g., including excessive bending, sharp corners, etc.).

SUMMARY OF THE INVENTION

An object of the present invention is to solve at least the above-described problems and disadvantages of the prior art.

Another object of the present invention is to provide an estimation of the 3D centerline for the catheter by implementing Bezier curves to interpolating points between 2D cross-sections to yield 3D reconstruction.

Another object of the present invention is to use a priori physical properties of line objects to increase reconstruction accuracy.

Another object of the present invention is to provide back projected angiographic information to achieve 3D reconstructions based on line object physical properties.

To achieve at least the above objects in whole or in part, an apparatus for determining three dimensional representations of a tortuous vessel according to the present invention includes an external information processing unit for receiving a first set of images of a line object in the tortuous vessel, determining external energy information of said first set of images and outputting the external energy information; an internal information processing unit for receiving internal information related to the line object, determining internal energy information of the line object and outputting the internal energy information; a 3D pullback path determination unit for receiving the external energy information and the internal energy information and determining a 3D pullback path; and a device for receiving the 3D pullback path and for calculating three dimensional representations of the tortuous vessel based on the 3D pullback path.

Additional advantages, objects, and features of the invention will be set forth in part in the description which follows and in part will become apparent to those having ordinary skill in the art upon examination of the following or may be learned from practice of the invention. The objects and advantages of the invention may be realized and attained as particularly pointed out in the appended claims.

BRIEF DESCRIPTION OF THE DRAWINGS

The invention will be described in detail with reference to the following drawings in which like reference numerals refer to like elements wherein.

DETAILED DESCRIPTION OF PREFERRED EMBODIMENTS

Figure 2:
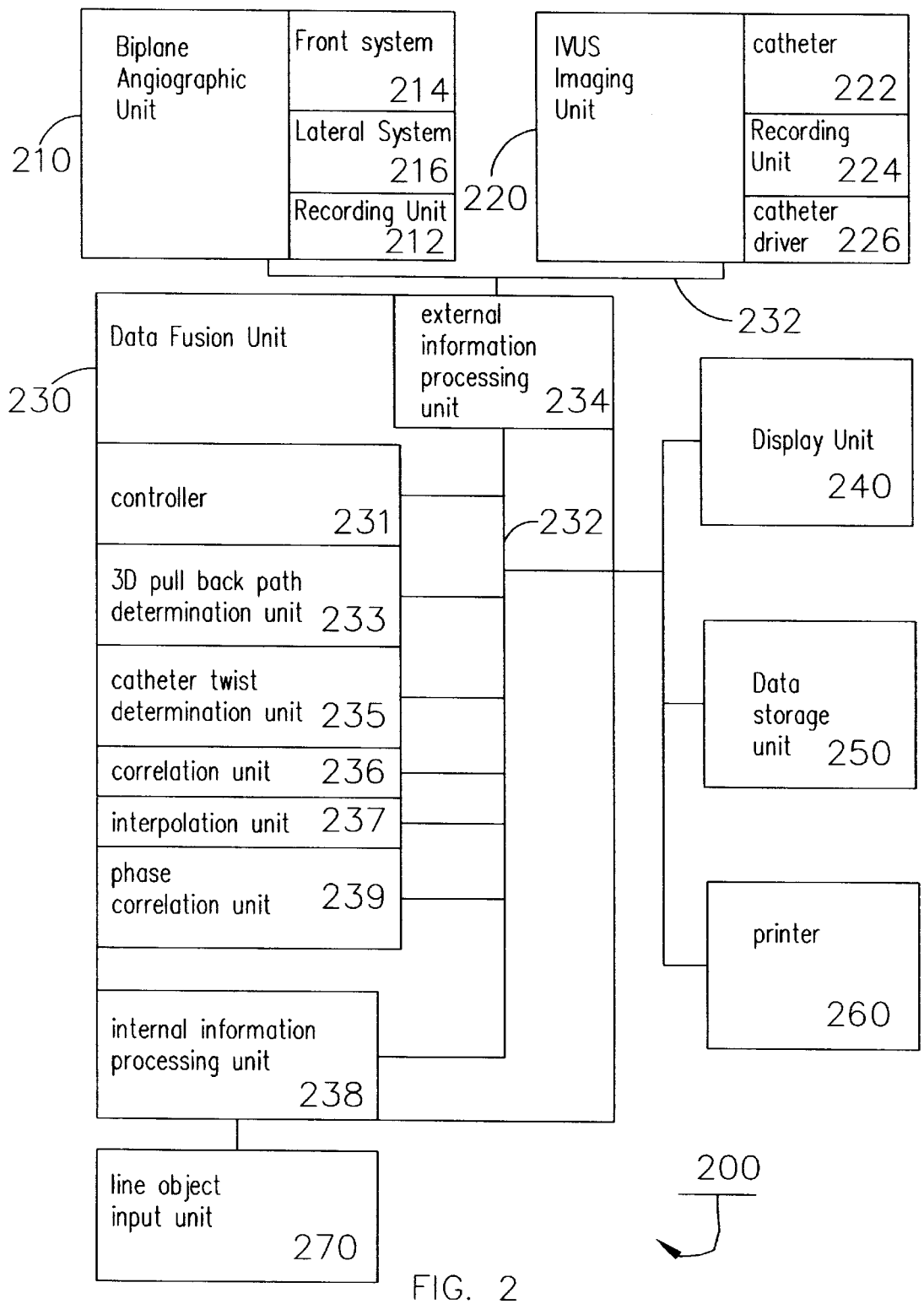
FIG. 2 is a diagram showing a preferred embodiment of an apparatus for determining 3D representations of tortuous vessels according to the present invention.

As shown in FIG. 2, a preferred embodiment of an apparatus 200 for representing tortuous vessels includes a biplane angiographic unit 210, an IVUS imaging unit 220, a data fusion unit 230, a display unit 240, a data storage device 250, a printer 260 and a line object input unit 270. The biplane angiographic unit 210 provides the angiograms of a designated tortuous vessel. The biplane angiographic unit 210 preferably includes both a frontal system 214 and a lateral system 216, each being the parallelogram type that can be rotated and angulated inside a gantry, as well as shifted independently inwards and outwards in a horizontal direction. Preferably, a prescribed distance between focal spot and isocenter can be adjusted and set. The biplane angiographic unit 210 provides fluoroscopy plus simultaneous recording in a recording unit 212 such as biplane recording on cine film.

The IVUS imaging unit 220 includes an IVUS catheter 222, a recording unit 224 and a catheter driver 226. The IVUS catheter 222 is preferably a sheathed catheter having a transducer located proximal to the distal tip of the imaging core. The IVUS images are recorded, for example, on VHS videotape with a rate of 30 frames/s in the recording unit 224.

As shown in FIG. 2, the data fusion unit 230 is preferably implemented on a programmed general purpose computer or workstation. However, the data fusion unit 230 can also be implemented on a special purpose computer, a programmed microprocessor or microcontroller and peripheral integrated circuit elements, an ASIC or other integrated circuit, a hardwired electronic or logic circuit such as a discrete element circuit, a programmable logic device such as a PLD, PLA, FGPA or PAL, or the like. In general, any device on which a finite state machine capable of implementing the flowcharts shown in FIGS. 3–6 can be used to implement the data fusion unit 230.

The display unit 240 is preferably a monitor or the like to display at least digitized visual and quantitative representations of the IVUS images, angiograms and 3D representations of a designated vessel respectively received from the IVUS imaging unit 220, the biplane angiographic unit 210 and the data fusion unit 230. The data storage unit 250 can store data for the data fusion unit 230. The printer 260 is preferably coupled to at least the data fusion unit. The line object input unit 270 allows the selection or input of features of a line object such as the IVUS catheter 222.

Figure 1:
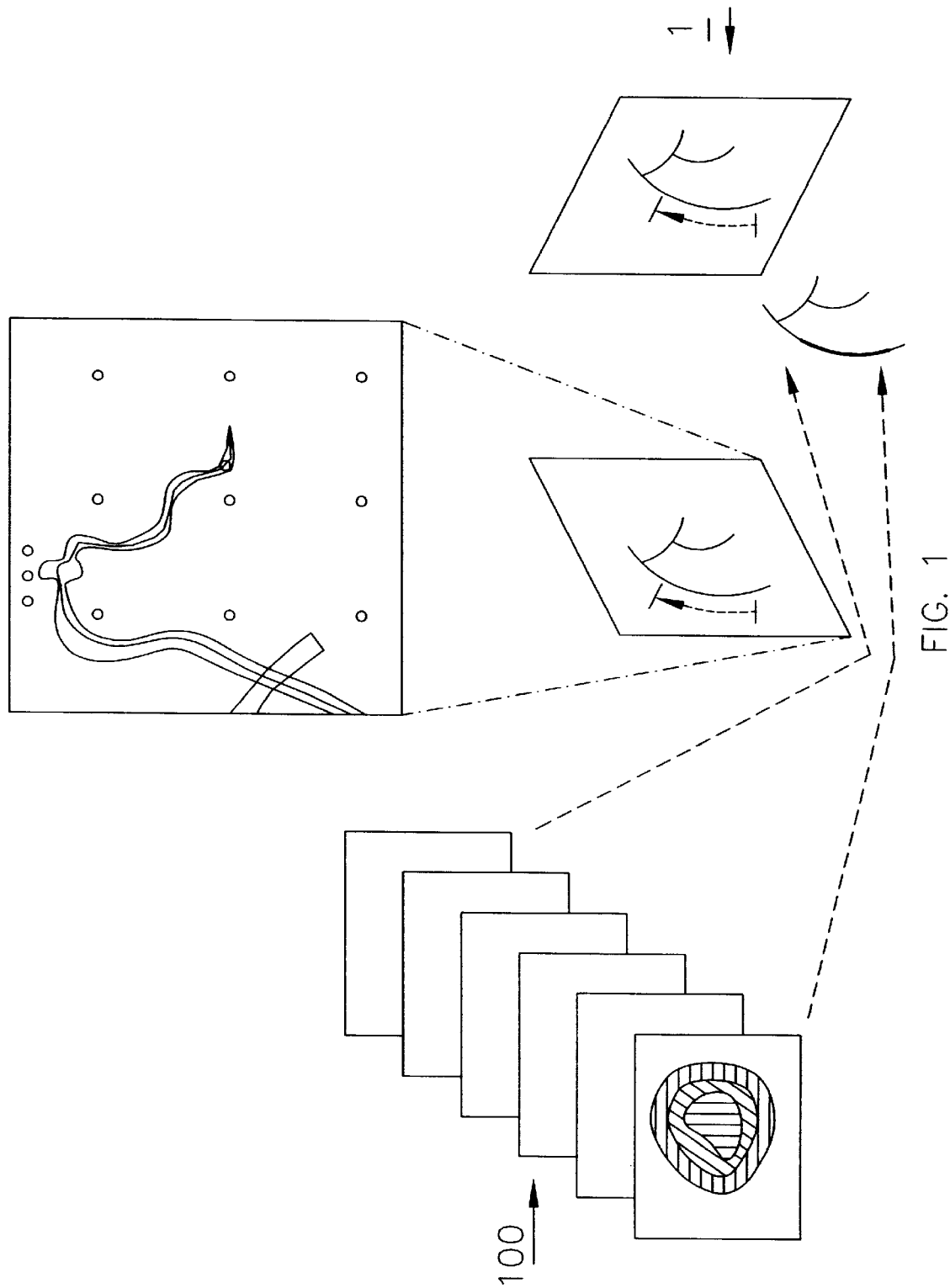
FIG. 1 is a diagram showing a 3D reconstructions using segmented cross sections of an IVUS pullback sequence and a vessel centerline of the 3D coronary tree vessel segment reconstructed from a biplane contrast angiogram.

Initially, the apparatus 200 obtains initial representations of the designated tortuous vessel. If required, the biplane angiographic unit 210 and the IVUS imaging unit 220 are calibrated during an initialization or setup. In initialization, an image geometry of the biplane X-ray gantry is actively calibrated with a calibration phantom prior to the examination. If the gantry has moved during the study, the calibration phantom has to be imagined in each new setting and the imaging geometries are derived off-line. For automated registration and correction of geometric distortion in the angiograms, semi-transparent markers can be affixed to the input screens of both image intensifiers. The semi-transparent markers can be used as an eight points grid as shown in FIG. 1.

To acquire the initial representations of the designated tortuous vessel, the IVUS catheter 222 is positioned at the distal end point of the designated vessel. Shortly before the pullback, biplane X-ray imaging is started to allow visualization of both the IVUS catheter 222 and the opacified vessel lumen. The IVUS catheter 222 is withdrawn at a fixed speed of about 1 mm/s with a pullback device such as the catheter driver 226. The catheter 222 uses an ultrasound beam to obtain and transmit preferably 30 images or frames/second. The five inch, seven inch or nine inch, for example, setup is imaged with the biplane angiographic unit 210 until the tip of the IVUS catheter 222 starts moving (for the elimination of backlash). The biplane angiographic unit 210 preferably obtains a final image when the IVUS catheter 222 stops moving to determine an endpoint of the pullback path. The initial representations (e.g., angiograms and IVUS images are then transmitted to the data fusion unit 230 or stored for future use.

The data fusion unit 230 preferably includes a controller 231, a data bus 232 a 3D pullback path determination unit 233, an external information processing unit 234, a catheter twist determination unit 235, a correlation unit 236, an interpolation unit 237, an internal information processing unit 238 and a phase correlation unit 239. The data bus 232 further preferably couples the elements of the apparatus 200 and the elements of the data fusion unit 230.

The controller 231 controls the operations of the data fusion unit 230. The 3D pullback path determination unit 233 then determines a 3D pullback path through the designated vessel. The pullback path can be determined from the IVUS catheter 222 or center points of the IVUS images. A centerline of the IVUS catheter 222 is preferably initially detected in a first biplane angiogram acquired after a transducer in the catheter 222 started to move backwards. A second biplane angiogram acquired after the catheter 222 stops moving can be used to determine an endpoint of the pullback path. If the IVUS catheter 222 is not present or not visible in the angiograms, both lumen borders are detected simultaneously in the angiograms and the lumen centerlines are determined. The IVUS images are segmented automatically into lumen, plaque, vessel wall, and adventitia in the IVUS imaging unit 220, or alternatively the unsegmented IVUS images can be transmitted to the data fusion unit 230 via the external information processing unit 234.

The 3-D pullback path determination unit 233 determines the pullback path of the IVUS catheter (sensor), which can be derived from the centerline of either the IVUS catheter or the vessel lumen. Preferably, the pullback path is reconstructed using a 3D evaluation of external information such as the biplane angiographic projections received from the external information processing unit 234 and the internal information such as the catheter 222 features received from the internal information processing unit 238. The resulting 3-D centerline polygon is smoothed and represented by a differentiable sequence of three-point Bezier curves (FIG. 11), which allow an adjustable degree of accuracy.

The line object input unit 270 can be used to enter the characteristics of a line object such as a catheter. The characteristics to be entered can include physical properties of the line object, which can then be used to determine a representation of its internal energy. The representation of the internal energy is preferably represented by a 3D curve or function. Thus, using a data entry method, a user can provide or be prompted for physical properties of the line object including modulus of elasticity, cross-sectional shape, diameter, wall thickness (for a hollow or composite line object), stiffness, minimum bend radius and temperature.

The line object input unit 270 or the data fusion unit 230 could then determine a 3D function representing the internal energy of the line object, which is used in determining the 3D pullback path by the internal energy processing unit 238 or the 3D pullback path determination unit 233.

Figure 10:
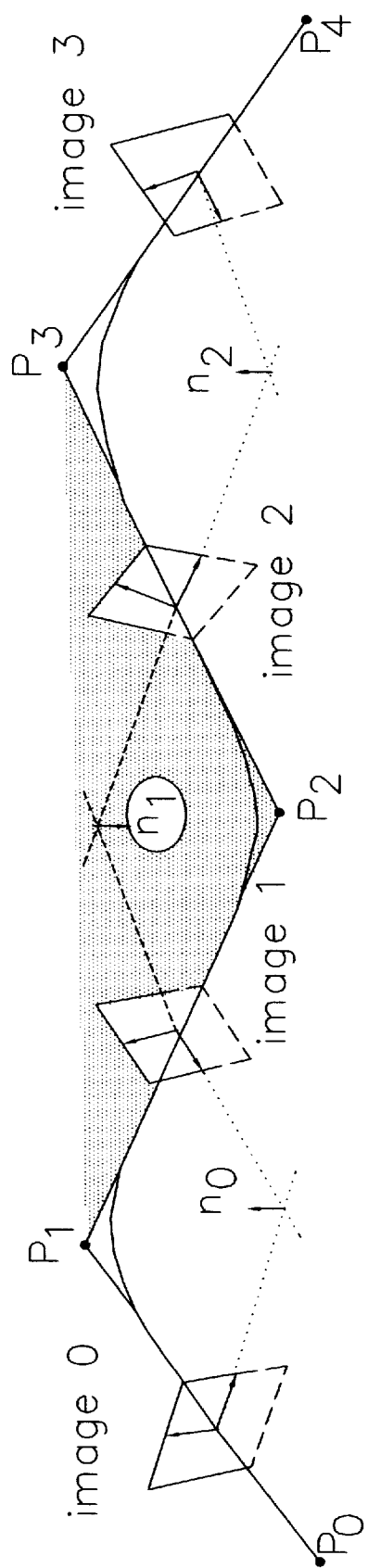
FIG. 10 is a diagram showing a 3D reconstructed lumen centerline polygon.

Following the 3D pullback path determination, the catheter twist determination unit 235 determines the tortuosity-induced twist of the IVUS catheter, which is derived from the previously reconstructed 3-D pullback path using an initial sequential triangulation shown in FIG. 10. The correlation determination unit 236 maps the segmented IVUS slices perpendicular to the 3-D pullback path according to the pullback speed and the determined twist pattern. Selected IVUS slices are rotationally adjusted using anatomic landmarks (e.g., vessel bifurcations) that are clearly discernible in both modalities.

The interpolation unit 237 fills the gaps between adjacent IVUS slices by sweeping the slices along the Bezier curves and by interpolating the signatures of the lumen, plaque, and wall contours in a polar coordinate system. The internal information processing unit 238 receives the features of the line object or the 3D representation of the line object from the line object input unit 270 as was discussed above.

The phase correlation unit 239 preferably uses the heart beat (ECG) and/or the breathing cycle (obtained during the initial representations) to obtain a time period or heart phase of interest that ensures the images from the IVUS catheter 222 inside the designated vessel are obtained under consistent conditions. Thus, the angiograms and IVUS images can be correlated with the ECG. However, the selected heart phase and the corresponding images can reduce the available IVUS images from 30 frames second.

Figure 3:
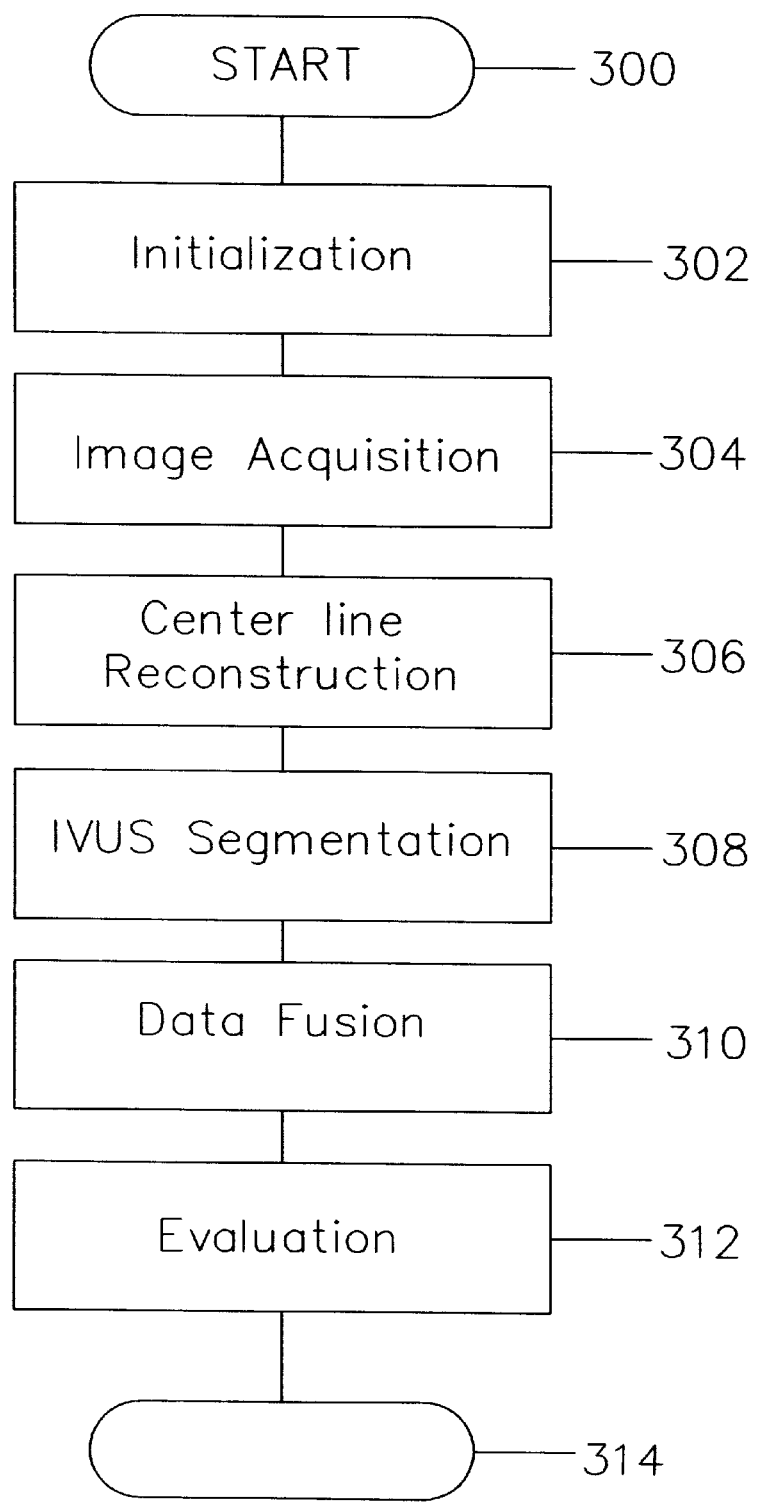
FIG. 3 is a diagram showing a preferred embodiment of a method for 3D representations of tortuous coronary arteries according to the present invention.

A preferred embodiment of a method for 3D representations of tortuous coronary arteries is shown in FIG. 3. The method shown in FIG. 3, for example, can be performed by the apparatus in FIG. 2. In FIG. 3, after starting in step 300, the process proceeds to step 302 where an initialization is performed. In the initialization, for example, a biplane angiographic unit is calibrated and a geometric correction is preferably performed.

During calibration, the biplane X-ray gantries are adjusted to a common isocenter using a calibration object that must by projected to the center of both image intensifiers (signifiers by the grids). The distance between the X-ray sources and the image intensifiers are derived from the projected diameter of the calibration ball utilizing the known distance of the isocenter from the X-ray sources. The scale at the imaging plane is indicated by the grid points in the geometrically corrected angiograms. The projection angles of the X-ray gantries are read out from the biplane angiographic unit imaging system.

During geometric correction a grid of eight equidistant metal markers is attached to the entrance screen of both the frontal and lateral image intensifiers for automated registration and correction of geometric distortion. The markers preferably span a square with a predetermined side length that can have its centroid adjusted to the center of the image intensifier and its side being vertically aligned using a level. A biquadratic correction polynomial is derived fully-automatically from the eight markers in the angiograms.

From step 302, the process continues to step 304. In step 304, image acquisition of the designated tortuous vessel is performed. During image acquisition, an IVUS pullback is acquired from the designated vessel. In the IVUS pullback, the IVUS catheter is preferably pulled back at constant speed using a mechanical pullback device. If not already available, the designated vessel is additionally imaged with a biplane X-ray system. In step 304, the IVUS catheter is positioned at the distal end of a pullback path in the designated vessel and preferably a first and second set of concurrent lateral and frontal biplane angiograms are recorded simultaneously on cine film. The first set of biplane angiograms is recorded to define an initial position of the IVUS catheter. The second set of biplane angiograms is recorded to define a final position of the IVUS catheter. The second set of biplane angiograms must be acquired at the same position of the cardiac cycle. If the pullback device however, provides a reliable distance measure, then the second set of biplane angiograms. Further, a diluted contrast agent can be injected into the designated vessel prior to the biplane angioagrams. Angiograms and IVUS pullback images are digitized and transferred preferably to the data fusion unit 30 workstation or the like. From step 304, control continues to step 306.

In step 306, a centerline of the vessel of interest is reconstructed. A 3D lumen centerline of the examined vessel is semi-automatically reconstructed from a geometrically corrected biplane angiogram. From step 306, control continues to step 308.

In step 308, the acquired IVUS pullback images are automatically segmented into lumen, plaque, vessel wall and adventitia. From step 308, control continues to step 310.

In step 310, data fusion between the IVUS pullback images and the corrected biplane angiogram are performed by the data fusion unit 230 according to the invention. Data fusion is described in detail below and in: "Geometrically Correct 3-D Reconstruction of Coronary Wall and Plaque: Combining Biplane Angiography and Intravascular Ultrasound," G. Prause et al. Conf. Computers in Cardiology, Sep. 8–11, 1996; "Accurate 3-D Reconstruction of Tortuous Coronary Vessels Using Biplane Angiography and Intravascular Ultrasound," G. Prause et al., SPIE Conf. Medical Imaging, Feb. 22–28, 1997; and "Towards a Geometrically Correct 3-D Reconstruction of Tortuous Coronary Arteries Based on Biplane Angiography and Intravascular Ultrasound," G. Prause et al., International Journal of Cardiac Imaging, No. 6, November/December, 1997 issue, the contents of all of which are hereby incorporated by reference. Data fusion preferably includes at least the process steps of catheter detection in 3D, reconstruction of the 3D pullback path, calculation of catheter twist, mapping, interpolation and rendering. The data fusion process step 310 will be described in detail below with reference to FIG. 4. From step 310, control continues to step 312.

In step 312, the 3D reconstructed designated vessel segment is visualized and quantitatively analyzed. From step 312, control continues to step 314 where the process is completed. As shown in FIG. 3, only the image acquisition, process step 304, is done simultaneously with the catherization procedures or cardiac interventions. All subsequent processing may be carried out independently at a later point in time.

Figure 4:
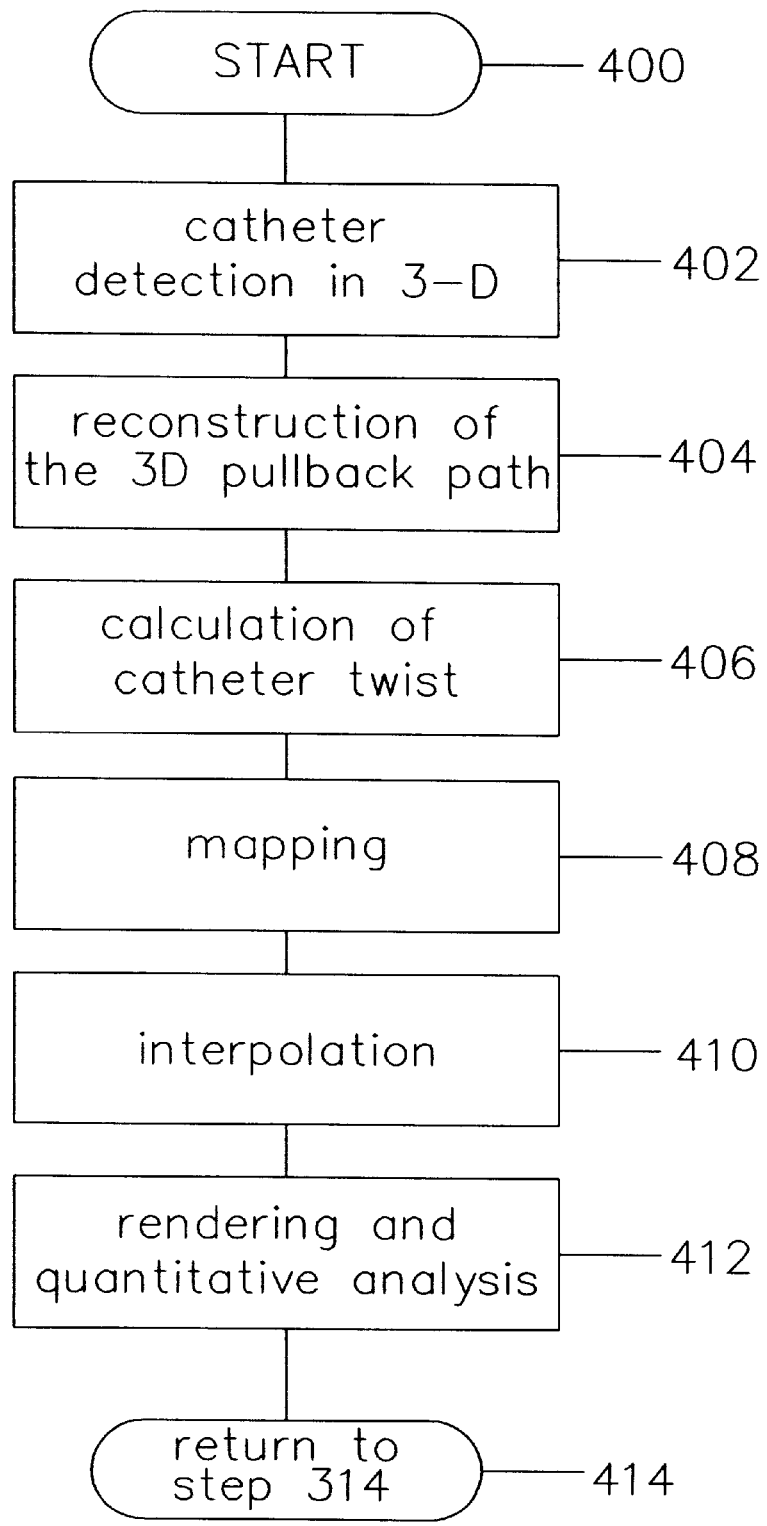
FIG. 4 is a diagram showing a preferred embodiment of a method for performing a data fusion process according to the present invention.

FIG. 4 shows a preferred embodiment of a method for performing the data fusion step 310. In FIG. 4, the process begins in step 400, where control continues to step 402. In step 402, catheter detection in 3D is performed. In the 3D catheter detection, back projected angiographic information is used to construct a 3D cost volume. Within this volume, the image core of the ultrasound catheter is detected as an optimal 3D spline curve considering imaging characteristics and physical properties of the catheter.

The back projected angiographic information includes, for example, physical properties of the line objects to be determined (e.g., the stiffness of the catheter, maximum achievable bending radius, etc.), which was input to the data fusion unit 230 using the line object input unit 270 and processed by the internal information processing unit 238. The 3D reconstruction benefits from the additional information because the internal information processing unit 238 processes the internal information relevant only to the line object (here the catheter 222) to determine together with the 3D pullback determination unit 233 only physically feasible 3D shapes of the reconstructed line objects in the catheter detection process. Previous catheter detection approaches did not consider such physical properties (internal information) and consequently often produced physically impossible catheter images.

The projection X-ray images used for biplane coronary angiography and fluoroscopy represent integrals of signal attenuation on the paths from the X-ray source to the specific points in the projection image. An exemplary projection image being an X-ray angiogram is shown in FIG. 1. Alternatively, the X-ray source can be any source creating a projection image or the 3D path may be known a priori. A 3D path may be predetermined in the case of industrial applications using blueprints or the like. Using at least two projection images with known epipolar geometry, the 3D line object is detected directly in the 3D data derived from the projection images. Further, the two projection images are not required to be orthogonal. Consequently, a 3D feasible object is determined directly in combined image data from projections instead of determining 2D projections from 2D data and subsequently combining the two projections into a 3D object in which the physical feasible cannot be guaranteed. From step 402, control continues to step 404.

Figure 5:
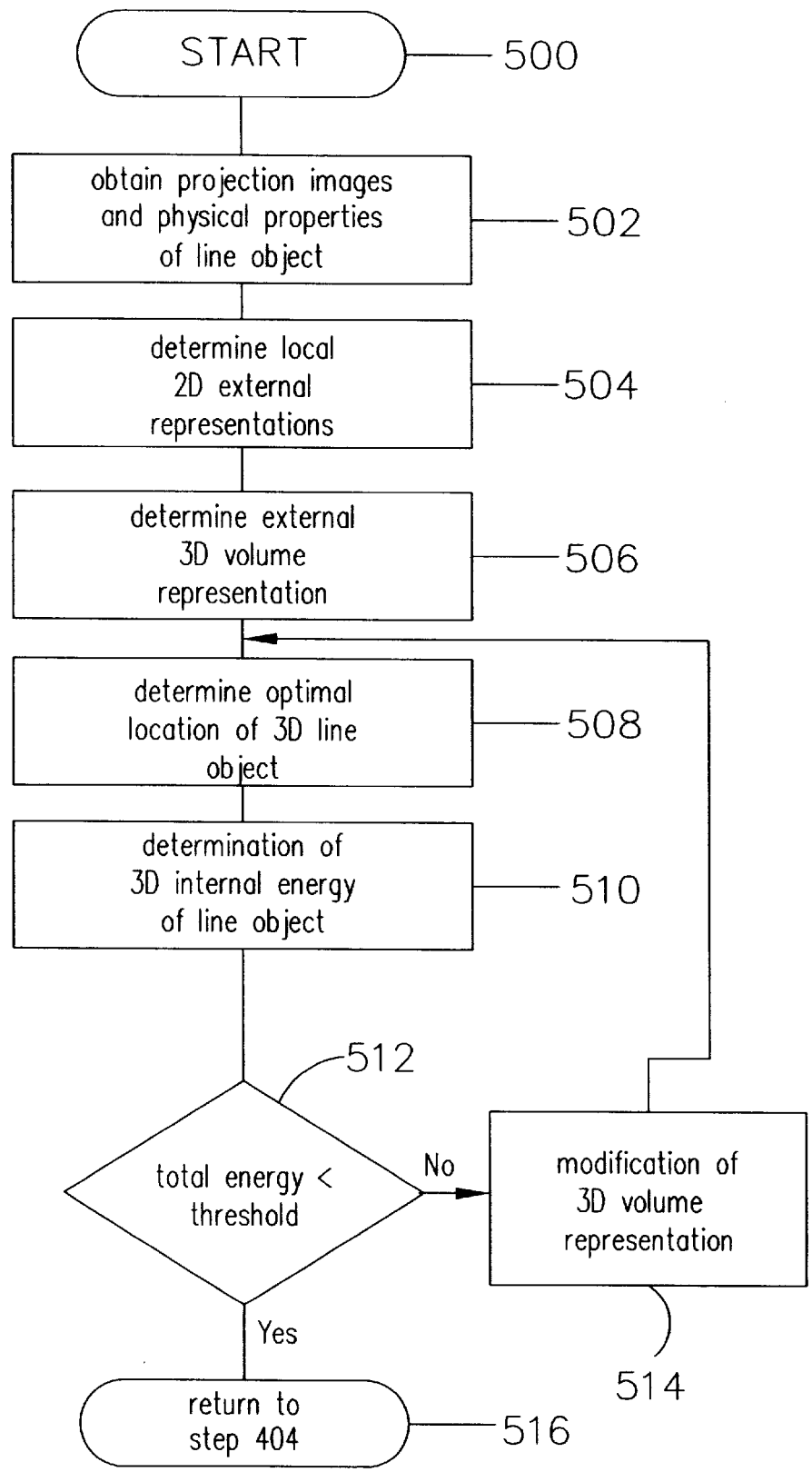
FIG. 5 is a diagram showing a preferred embodiment of a method of direct 3D line object detection from projection images according to the present invention.

FIG. 5 shows a preferred embodiment of a method performed by the data fusion unit 230 including internal information processing unit 238, external information processing unit 234 and the 3D pullback path determination unit 233 for determining direct 3D line object detection from projection images according to the present invention. The preferred embodiment disclosed in FIG. 5 can be used for the 3D catheter detection step 402. In FIG. 5, the process begins in step 500, where control continues to step 502. In step 502, the projection images and the physical properties of the line object are obtained from the line object input unit 270 and the internal information processing unit 238. From step 502, control continues to step 504. In step 504, local cost values $P(x,z)$, $P(y,z)$ are derived from the 2D angiography images to reflect image properties of the line object to be determined using external information processing unit 234 and the 3D pullback path determination unit 233. For example, if the line object in 2D image is known to be bright, the local 2D cost value may correspond to the local image brightness. Following this method, the more probable the image location, the lower the representation value (e.g., external energy or cost). The brighter pixels in the 2D angiography image will correspond to low local representation values. The choice of image properties to be used for local value determination depends on image properties of the line object in question and may include among others brightness, local edge magnitude, local edge direction, etc. The local representation values $P(x,z)$, $P(y,z)$ are preferably organized in a form of a matrix $P_I$, $P_{II}$ of the set of biplane X-ray projectional angiographic images. From step 504, control continues to step 506.

In step 506, an external energy 3D representation volume is constructed using projection geometry parameters of the angiographic biplane image acquisition system. The term external energy is used to indicate that the partial representations originate in the image, not in the physical properties of the line object itself. Using the local 2D representation values, P(x,z), P(y,z), the 3D representation volume elements C(x,y,.z) are described as follows:

C(x,y,z)=F[P(x,z), P(y,z)]

where F[__] is a function that combines grey level values of the two angiographic images according to the projectional geometry parameters of the actual biplane image acquisition setup. In the simplest case of orthogonal projection and using same-size images, the 3D representations are described as follows:

F[P(x,z), P(y,z)]=((P(x,z))(P(y,z))).

Thus, in the orthogonal case, the two local 2D representations were combined by direct multiplication. In non-orthogonal cases, the function can combine corresponding local representations according to previously determined epipolar geometry. Similarly, if images are not the same-size images, the representations can initially be scaled to a common image size. Many other operators and/or arrangements of operators combining the tow corresponding local representations can be used. The general case using the 2D representations matrices $P_I$, $P_{II}$ can be expressed as follows:

C(x,y,z)=G{H[$P_I$, $P_{II}$]} where G is an operator (arrangement of operators) combining the local representations and H is a function determining corresponding local representations according to the epipolar geometry. Thus, the 3D volume of external energy representations is determined in step 506. From step 506, control continues to step 508.

In step 508, an iterative optimization process is started. Three-dimensional graph search based on 3D dynamic programming determination, heuristic 3D graph search or similar global minimization (e.g., total energy, cost, etc) technique is used to determine the optimal location of the 3D line object according to the current 3D volume values. Thus, the search space is represented by the 3D cost volume where the values of this volume represents external energy and a priori physical properties of the line object represent the line object internal energy. From step 508, control continues to step 510.

In step 510, a 3D curve representation (a Bezier curve, or the like) of the current 3D line object is determined. The local internal energy representations of the current iteration along the 3D Bezier curve representation is determined considering the a priori known physical properties of the line object, which can be entered using, for example, the line object input unit 270. The internal energy is determined locally along the line object (e.g., if the line object is known to be stiff, any sharp bending will result in locally high internal energy of the line object). An exemplary equation that describes the internal energy $E_{int}$ of a parametrically defined curve v(s)=[x(s), y(s), z(s)], where x,y,z are coordinates along the curve and s ϵ[0,1] follows:

$E_{int}=\alpha(s)|dv/ds|^2+\beta(s)|dv^2/ds^2|^2$ where α(s), β(s) specify the elasticity and stiffness of the curve. From step 510, control continues to step 512.

In step 512, the global and local internal energy of the currently determined line-object is assessed. If neither the global, nor the local energies exceed a prescribed threshold, the line object is considered final and control continues to step 516. Otherwise, control continues to step 514. In step 514, the current 3D representation volume (most recently determined) is modified to incorporate the local 3D internal energy representations. The modification increases the local 3D energy representation in neighborhoods of the current line object as a function of its local internal energy. The rational is to force the shape of the 3D line object to find an optimal compromise location of the line object in 3D space that would both agree with the external representations (image data) and the internal representations physical properties of the resulting line project). After the modification of the 3D volume, control returns from step 514 to step 508, where another iterations of the optimization process is performed. In step 516, control returns to step 404.

Thus, as shown in FIG. 5, construction of a 3D cost volume from two (or more) projections and optimal detection of the 3D line object within the 3D cost volume are two key features in determining direct 3D line object detection from projection images.

As a result of fully 3D optimal detection of line objects, the determined line objects satisfy their a priori physical properties and an increased final reconstruction accuracy can be achieved compared to previous two-dimensional approaches.

Referring back to FIG. 4, in step 404, reconstruction of 3D pullback path is performed. In reconstruction of the 3D pullback path, starting and end points of the pullback are respectively manually identified in initial and final geometrically corrected angiograms respectively based on the first and second angiograms. The 3D pullback path of the IVUS catheter is reconstructed from the biplane angiograms using a spline-based 3D minimization approach. During catherization, IVUS images are acquired perpendicular to and along the 3D pullback trajectory of the IVUS transducer (pullback path). Consequently, the images must be mapped back perpendicular to the 3D pullback path with the image centers (e.g., respective location of the transducer in the IVUS catheter) intersecting the pullback paths. To achieve a correct positioning and orientation of the IVUS images in 3D space, the actual pullback path has to be recovered from the biplane angiograms as accurately as possible.

Thus, the pullback paths in the biplane angiograms are preferably determined in first and second images acquired at the beginning and at the end of the pullback with the centerline of the IVUS catheter used as the pullback path. The second biplane angiogram taken at the end of the pullback at the same heart phase would be of additional value since it shows the final position of the transducer and allows comparison between reconstructed and measured pullback length. In cases where the IVUS catheter is not present or identifiable in the angiograms, the lumen centerline may be taken as a less accurate fallback solution. Alternatively, the pullback path can be determined in a sequence of biplane angiograms recorded over the entire IVUS catheter pullback length that directly follow the location of the transducer. However, reconstructing the transducer path from dynamic biplane angiograms recorded during the entire pullback disadvantageously increases the radiation dose for both the patient and the laboratory personnel and requires additional work during image acquisition and reconstruction. Further, the accuracy gain reported for in-vitro settings is impeded by heart motion, patient movement, and breathing in a clinical setting.

Figure 6:
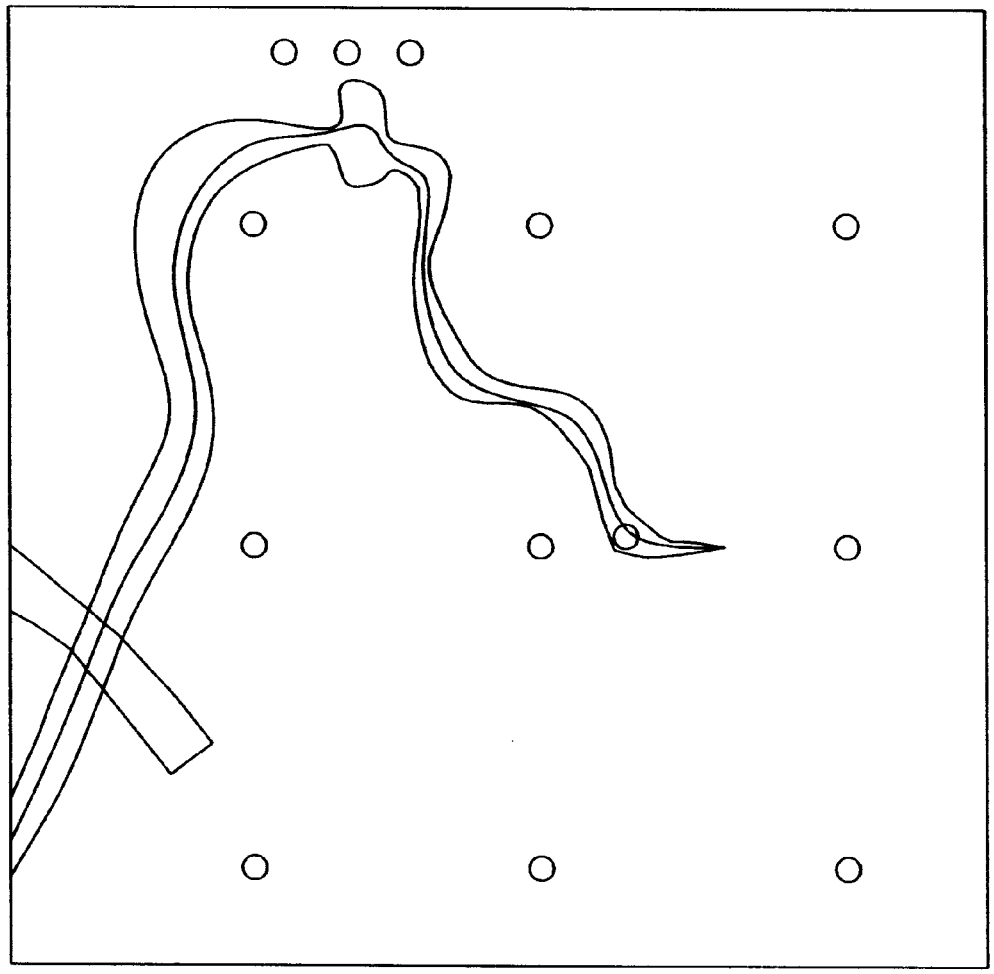
FIG. 6 is a diagram showing an exemplary (X-ray angiogram) projection image.

Further, the pullback path can be reconstructed directly using the IVUS catheter's shadow in the angiograms, or indirectly via the lumen catheter within the dye-filled coronary vessel lumen as shown in FIG. 6. Note the shortcuts taken by the catheter in FIG. 6. However, not always is the IVUS catheter available or visible. Sometimes, the IVUS catheter shadow is overshadowed by the contrast agent, or it might not even be present in the angiograms (e.g., if one wants to combine IVUS images and biplane angiograms from separate studies).

Figure 7:
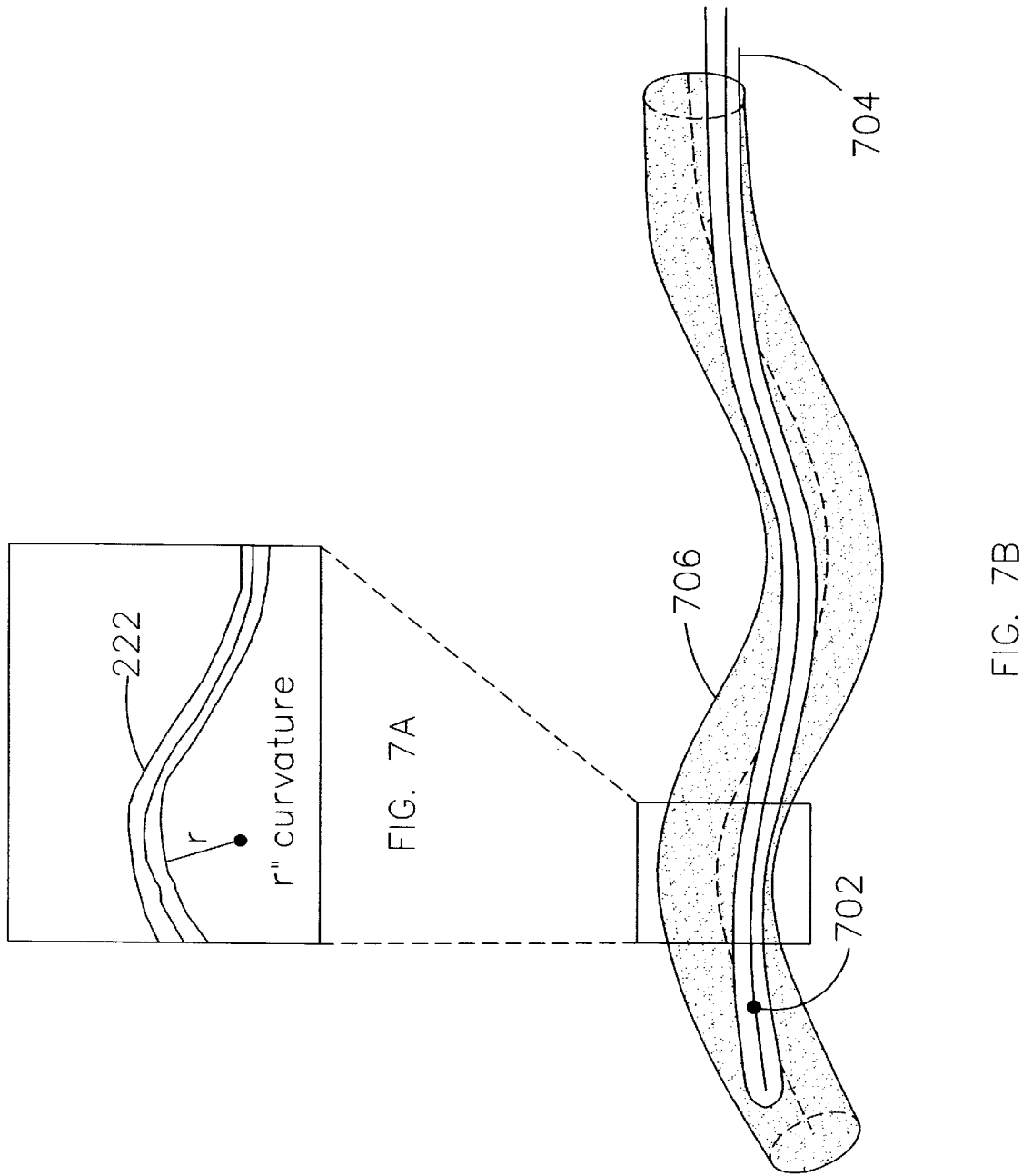
FIGS. 7A–7B are diagrams respectively showing a catheter and a catheter in a tortuous vessel.

In these cases, the lumen centerline is a less accurate but available approximation of the pullback path. Then, the IVUS frames are oriented with their lumen centroids perpendicular to the biplane reconstructed 3D lumen centerline. This approach can be related art automated vessel contour detection methods, which are known to one of ordinary skill in the art. However, as shown in FIG. 7B, the IVUS catheter 222 including a transducer 702 and a sheath 704 tends to take a position of minimum bending energy inside a tortuous vessel. As shown in FIG. 7A, the second derivative r" of the 3D curve representing the catheter 222 is one parameter which describes curvature and can be merged with internal energy information to determine feasible catheter positioning of the line object. When the transducer 702 is pulled back during image acquisition, the lumen centerline shown as a dotted line in vessel lumen 706 in FIG. 7B can deviate in position and direction from the actual pullback path. An angular error occurs whenever the catheter centerline is off the lumen centerline, and the length of the reconstructed lumen centerline exceeds the length of the actual pullback path. From step 404, control continues to step 406.

Figure 8:
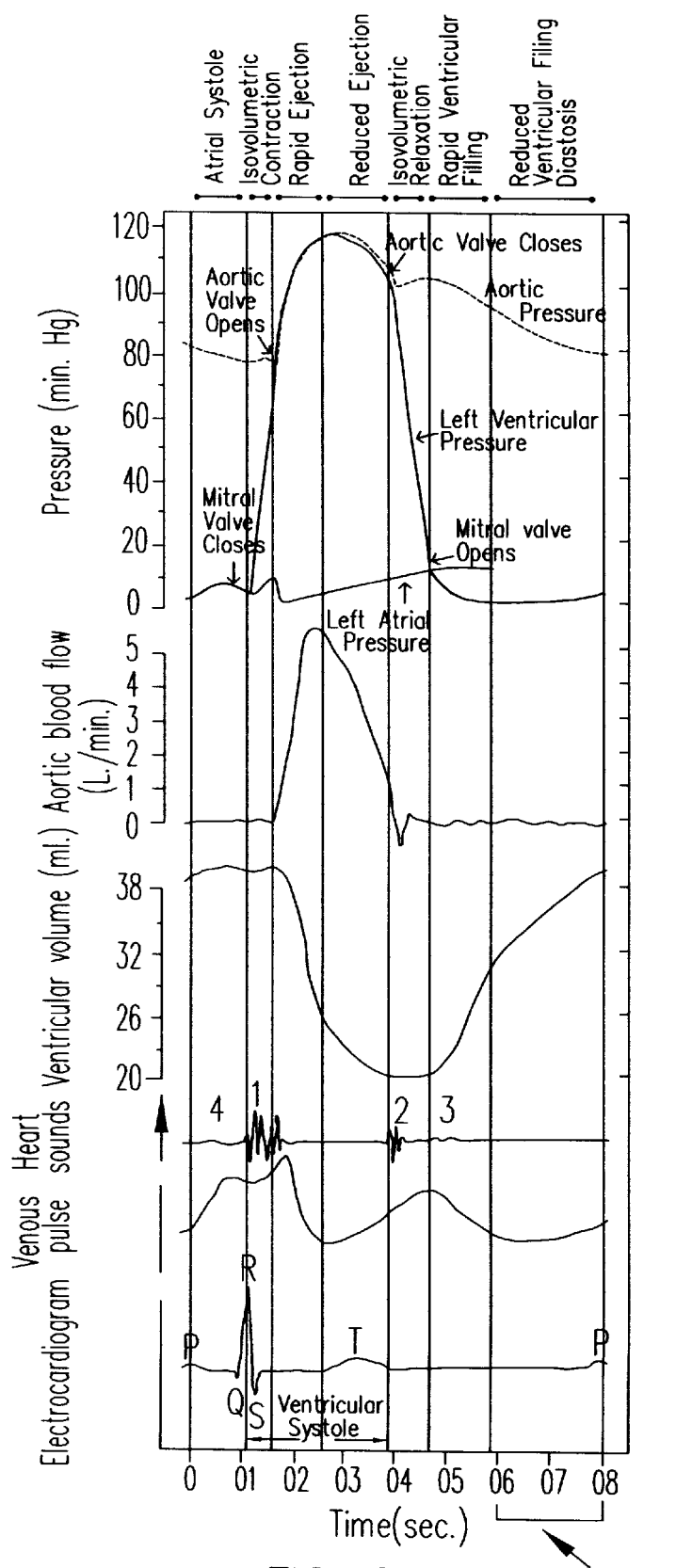
FIG. 8 is a diagram showing representative heart motion.

In step 406, calculation of the catheter twist is performed. In calculating the catheter twist, the radial twist of the IVUS catheter during pullback is derived from the 3D pullback path. The overall rotational orientation is obtained from anatomic landmarks (e.g., vessel bifurcations) and the eccentricity of the catheter in the IVUS pullback images. Longitudinal catheter twist is systematic inter-frame distortion that affects the rotational orientation of the IVUS frames along the pullback path. As a result, coronary plaque may be, for instance, reconstructed at the innerside of a vessel bend while it is actually located at the outer bend with different hemodynamic consequences. Systematic catheter includes catheter twist caused by heart motion and breathing as well as catheter twist that is induced by the tortuosity of the pullback path. The influence of heart motion and breathing in an in-vivo setting may be largely suppressed by gated image acquisition as shown by FIG. 8. Further, a sheathed type of catheter employed offers good positional stability in an in-vivo coronary system as judged from ECG-gated biplane angiograms.

By incorporating ECG-gating, a time window 800 of minimal heart motion can be determined and obtained from the IVUS pullback images. As shown in FIG. 8, left atrial, aortic and left ventricular pressure pulses are correlated in time with aortic ventricular volume, heart sounds, venous pulse, and electrocardiogram for a complete representative cardiac cycle. However, implementing the ECG-gated approach can limit the number of available images from the IVUS pullback images.

Figure 9:
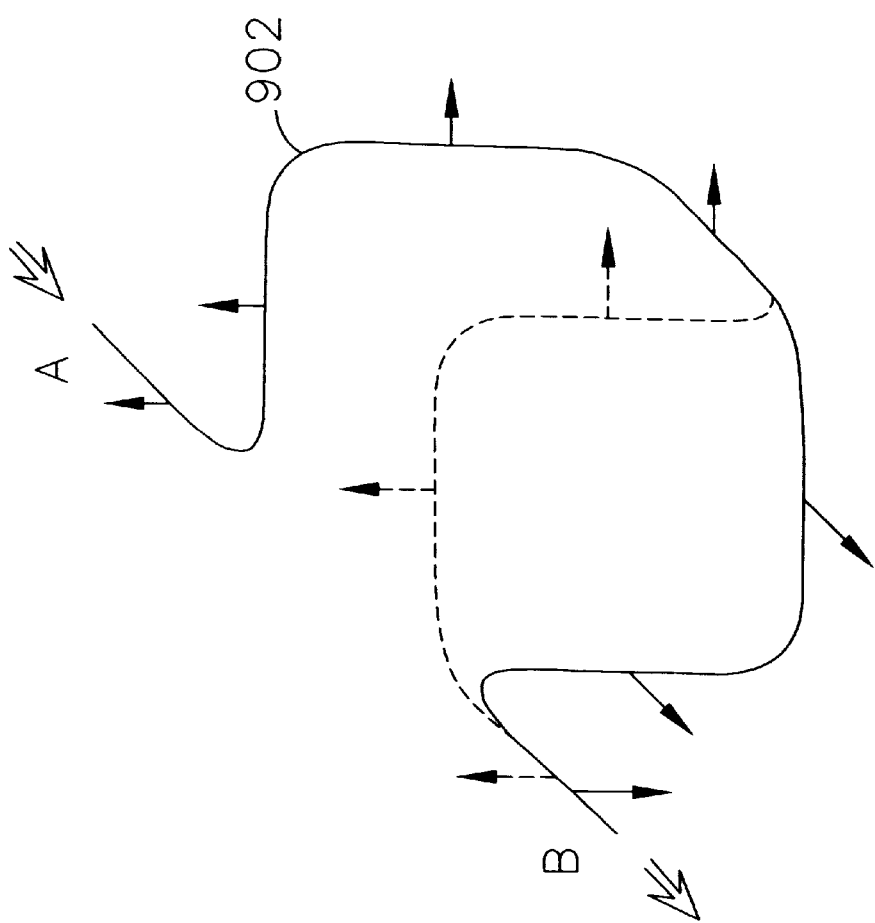
FIG. 9 is a diagram showing tortuosity-induced catheter twist.

As the catheter is pulled back along a nonplanar 3D path, the rotational orientation of the IVUS catheter/images depends on the previously traversed trajectory. This effect is illustrated in FIG. 9 for a pullback along the edges of a cube assuming a catheter with a torsion-free drive cable and obeying the laws of differential geometry. As the catheter is pulled back, the local "upright" orientation of the transducer (indicated by short vectors) may change within the global coordinate system whenever the IVUS transducer enters a new plane in space. For the solid pullback path 902, the initial orientation at the beginning of the pullback (point A) is rotated by 180° at the end of the pullback (point B). If the IVUS transducer follows the dashed pullback path 904 trajectory, however, the final orientation equals the initial one (Point A).

The tortuosity-induced catheter twist shown in FIG. 9 can be determined from the reconstruction pullback path. As shown in FIG. 10, for the first five points $P_0, \ldots, P_4$, the 3D reconstructed polygon representing the pullback path is triangulated always taking three consecutive points $P_i, P_{i+1}, P_{i+2}$ at a time. The IVUS images i and i+1 are located halfway between $P_i, P_{i+1}, P_{i+2}$ at points $S_i=(P_i+P_{i+1})/2$ and $S_{i+1}=(P_{i+1}+P_{i+2})/2$. The images are perpendicular to the tangent vectors $t_i=P_{i+1}-P_i$ and $t_{i+1}=P_{i+2}-P_{i+1}$. The orientation of IVUS images i+1 is determined from the already known orientation of image i by the following inductive method:

1) The center of the circumscribed circle of the triangle defined by $T_i=(P_i, P_{i+1}, P_{i+2})$ is determined as the intersection of the perpendicular bisectors of the tangent vectors $t_i$ and $t_{i+1}$;
2) The orientation of image i+1 is determined by rotating image i around the normal vector $n_i=t_i \times t_{2+1}$ of the triangle $T_i$; and
3) The center of image i+1 is shifted to tangent vector $t_{i+1}$ since the perpendicular bisectors are generally not equal in length.

The 3D reconstructed pullback path $P_0, \ldots, P_4$ is preferably approximated by a sequence of adjustable 3-point Bezier curves. From step 406, control continues to step 408.

In step 408, mapping is performed. In mapping, a discrete 3D data volume (voxel cuboid) is generated and the IVUS images are mapped perpendicular to the 3D pullback path. The spacing of the images is defined by the pullback speed. The rotation angle between adjacent images and the overall rotational orientation is given by the result of step 404, reconstruction of the 3D pullback path. From step 408, control continues to step 410.

In step 410, interpolation is performed. In the interpolation, first biplane reconstructed 3D polygon representing the lumen centerline is approximated by a sequence of 3-point Bezier curves with repetitive center points. Second, borders between lumen, plaque, vessel wall, and adventitia are interpolated between consecutive 2D IVUS slices. Third, interpolated cross-sectional IVUS slices are swept along the Bezier-approximated vessel centerlines to produce the 3D vessel reconstruction.

Figure 11:
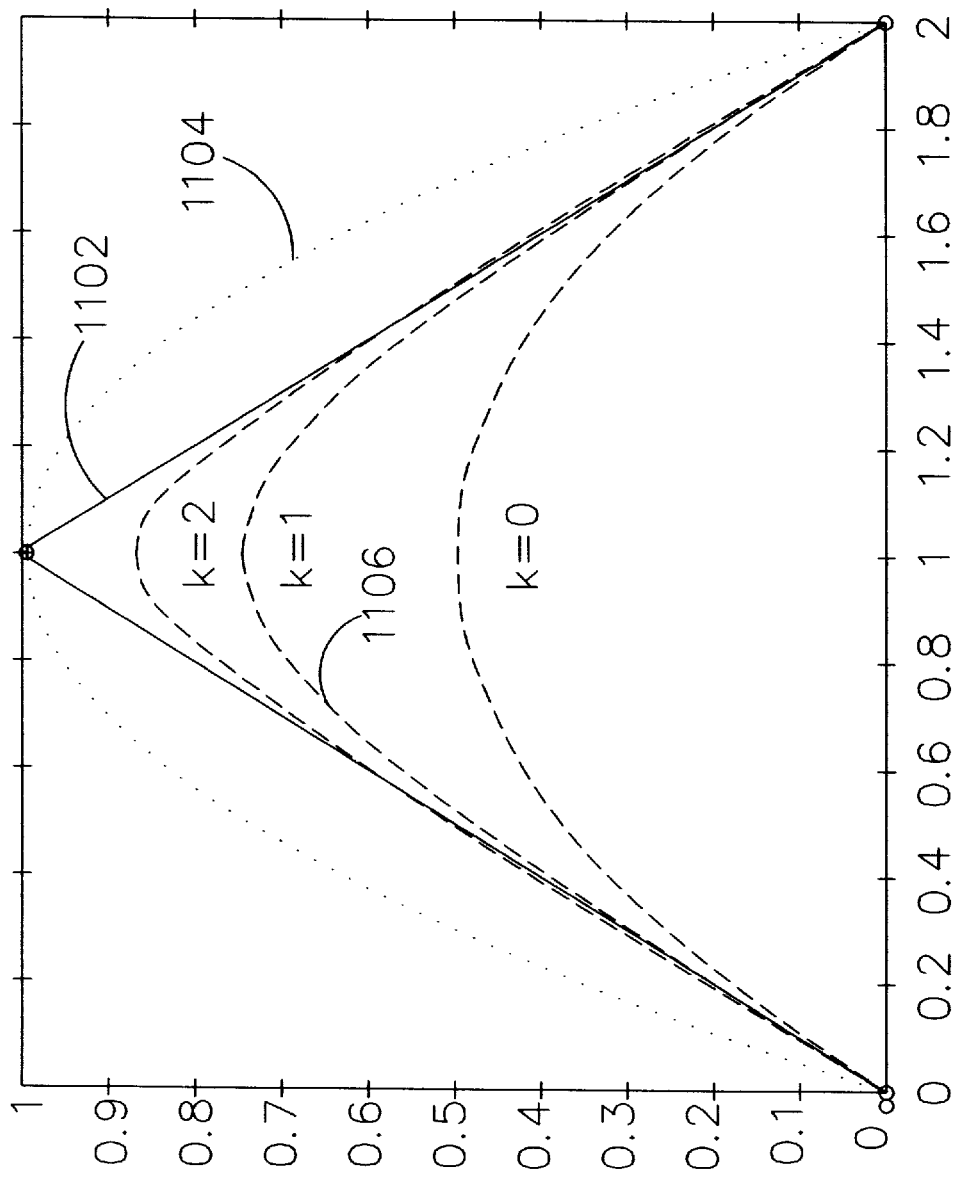
FIG. 11 is a diagram showing a series of Bezier curves.

The 3D reconstructed lumen centerline polygon resulted in problematic representations, and in particular, in problematic representations at locations approaching and approximating vertices between linear segments. While positioning of the IVUS slices in the vertex area appeared to be a local distortion that could be overcome by local approximations, the invertors determined that a local average such as a moving average filter did not represent the behavior of the catheter 222. The local behavior in the area of the vertices was determined to be representable by a global approximation of the behavior of the entire line object. Thus, the global approximation of the internal energy of the line object represented the behavior of the catheter better than local smoothing methods. Accordingly, the 3D reconstructed lumen centerline polygon is approximated by a sequence of 3-point Bezier curves with repetitive center points in order to provide a smooth and differentiable centerline representation 1106 as shown in FIG. 11. The i-th Bezier curve segment $b_{i,k}(w)$ and the first derivative of the i-th Bezier curve segment with parameters $w \in [0,1]$, starting point $S_i=(P_i+P_{i+1})/2$, endpoint $S_{i+1}=(P_{i+1} P_{i+2})/2$, and control point $P_{i+1}$ with k repetitions is described by as follows:

$$b_{i,k}(w)=(1-w)^{k+2}S_i+[1-W^{k+2}-(1-W)^{k+2}]P_{i+1}+w^{k+2}S_{i+1}$$

$$b'_{i,k}(w)=-(k+2)(1-w)^{k+1}S_i+(k+2)[(1-w)^{k+1}-w^{k+1}]P_{i+1}+(k+2)w^{k+1}S_{i+1}.$$

Advantageously, the Bezier curves can be adjusted to a desired degree of accuracy through repetition of the inner control point. Thus, the Bezier curves increase the efficiency of the designated vessel centerline determination. FIG. 11 shows Bezier curves with control points (0,0), (1,1), (2,0) and k=0,1,2 repetitions of point (1,1). As shown in FIG. 11, with just one repetition (k=1), the polygon through the control points (solid line) is better approximated by a Bezier curve 1106 than by a cubic spline 1104 (dotted line). Further, the Bezier curves allow the small number of ECG-gated IVUS slices to accurately determine the designated vessel centerline determination.

The interpolation between two consecutive segmented IVUS slices are carried out in a polar coordinate system. The borders between lumen, plaque, vessel wall, and adventitia are transformed into a signature (e.g., angle-distance representation) with reference to the vessel centroid. Unknown signatures located between two given ones are interpolated through weighted averaging. In the signature space, a twist of an IVUS slice corresponds to a cyclice shift of the respective signature. Finally, the 3D reconstruction of the designated vessel is generated by sweeping the interpolated IVUS slices along the Bezier-approximated lumen centerlines.

Thus, gaps between adjacent IVUS slices are filled using a fast spline-based interpolation algorithm. The interpolation is especially adapted to the application domain and differs from standard interpolation approaches in how corresponding image points are detected and utilized in the interpolation process. Catheter twist results and 3D catheter trajectory are considered. From step 410, control continues to step 412.

In step 412, rendering is performed. In rendering, the voxed cuboid representing the 3D vessel reconstruction is rendered interactively. From step 410, control continues to step 414, where control returns to step 314.

Figure 12:
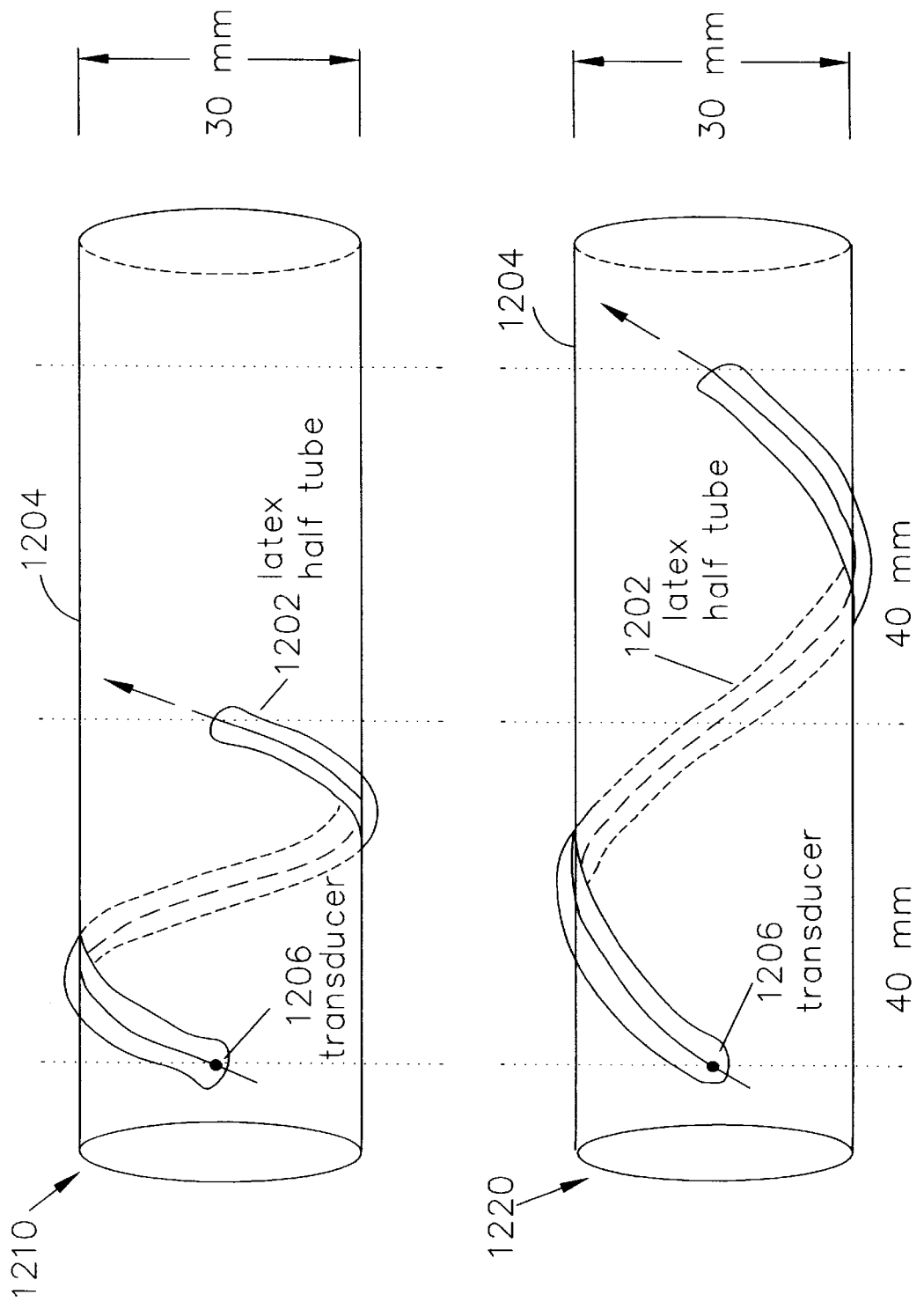
FIG. 12 is a diagram showing helical vessel phantoms.

The correctness of the twist calculations using the preferred embodiments of the apparatus and method for determining 3D representations of tortuous vessels was validated using two helical vessel phantoms as shown in FIG. 12. A latex half tube 1202 was wrapped around a cylinder 1204 of 30 mm in diameter to form a helical pullback path. A short helix 1210 had a displacement of 40 mm per revolution and a pullback length (measured and calculated) of 105 mm. A long helix 1220 had a displacement of 80 mm (twice as much) with a pullback length of 126 mm. Both setups were immersed into water at body temperature and the catheter sheath was flushed periodically to remove air bubbles. A catheter including transducer 1206 was withdrawn at approximately constant speed showing a cross-section view of the latex half tube and the attached cylinder wall. Catheter twist was determined by measuring the rotational orientation of the cylinder wall in the IVUS pullback images.

Figure 13:
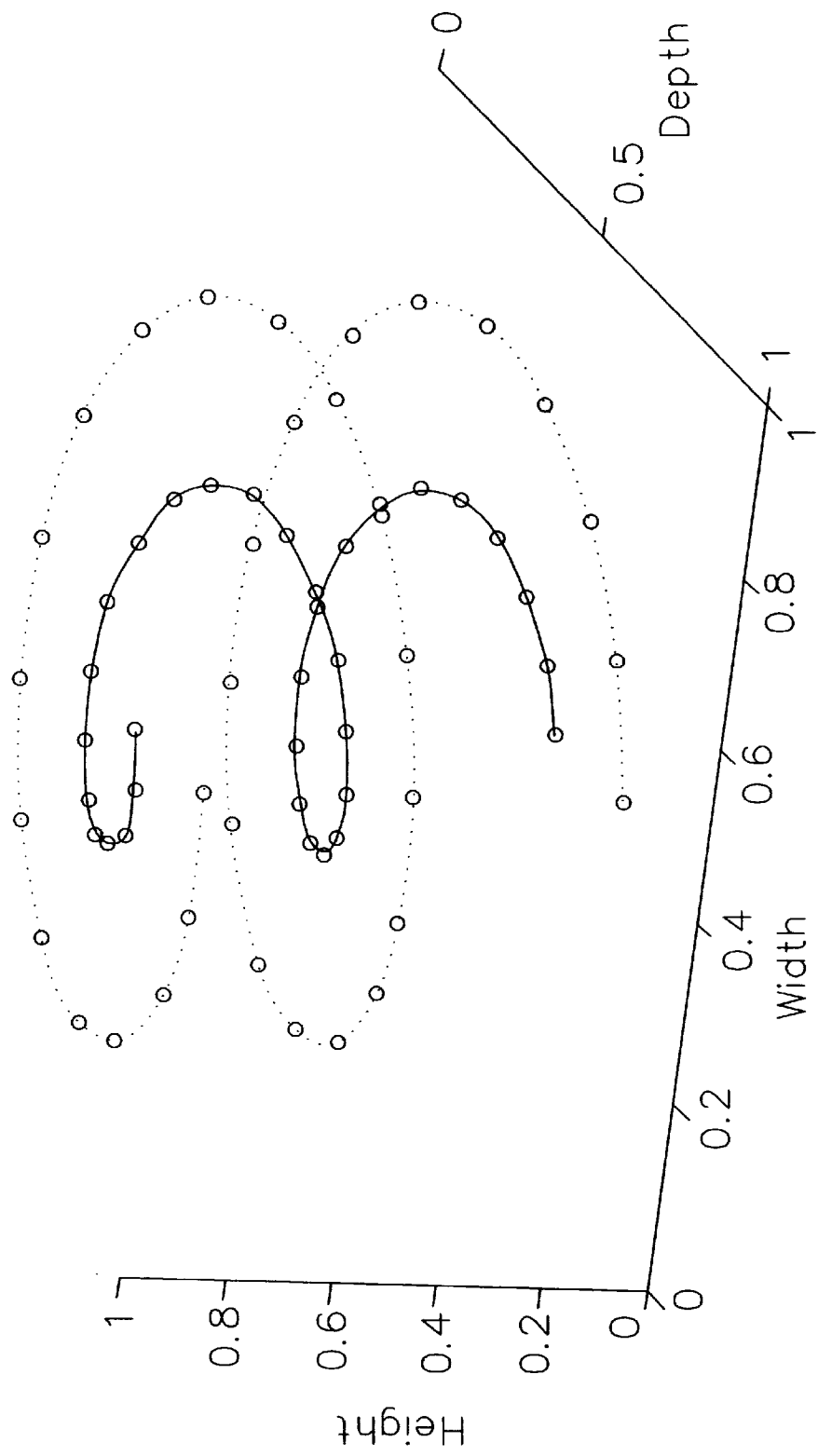
FIG. 13 is a diagram showing simulations for two helical pullbacks.
Figure 14:
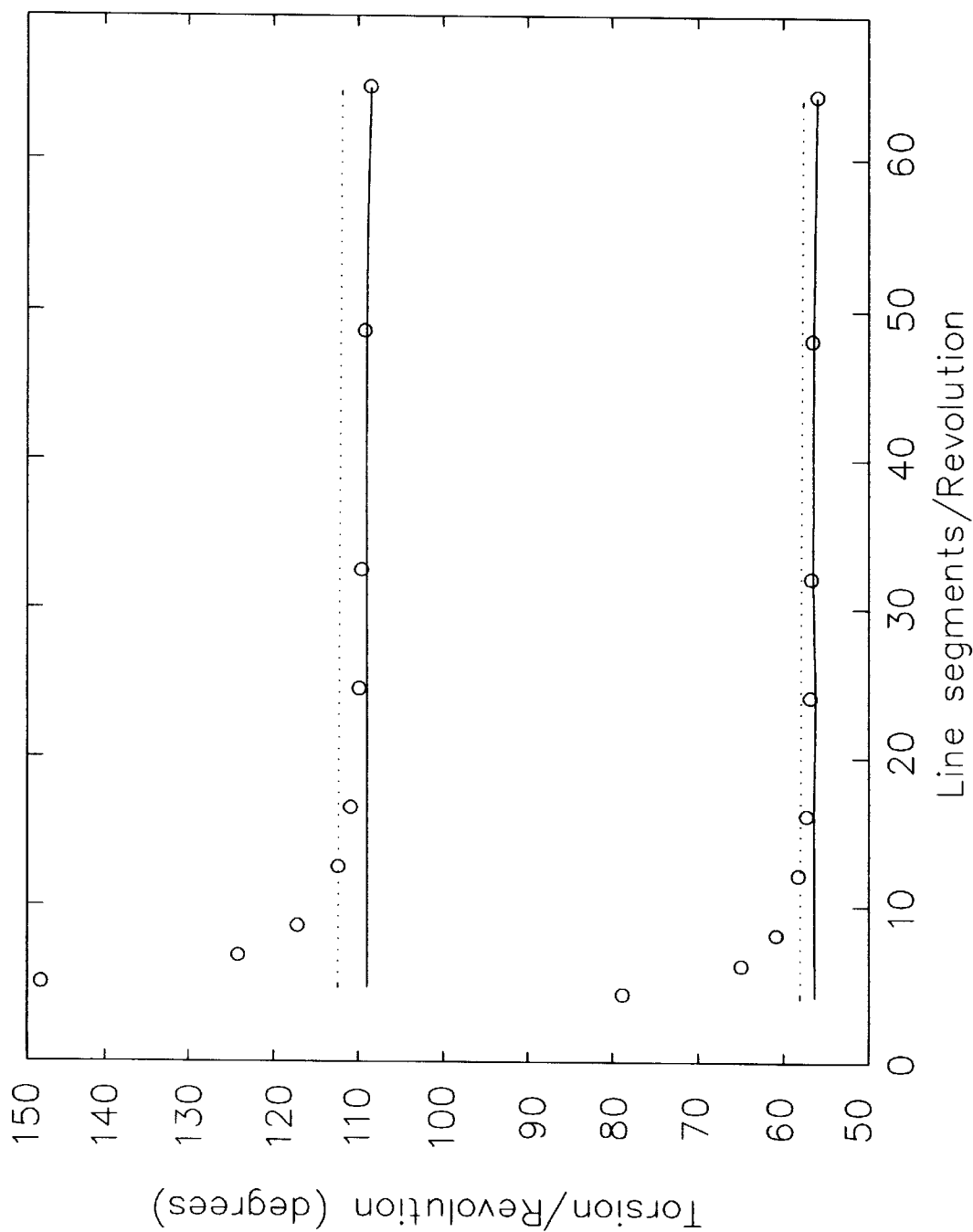
FIG. 14 is a diagram showing measured catheter twist for two helical pullbacks.

The observed twist of the IVUS catheter was exactly as predicted in computer simulations. Computer simulations for two helical pullbacks of two full revolutions shown in FIG. 13 were defined by two concentric 3D polygons within a unit cube of arbitrary units (a.u.). The number of line segments per polygon were varied between 8 and 128 to study the error introduced by sampling. As shown in FIG. 13 for the polygons with 32 line segments, both helical pullbacks had the same displacement per revolution (0.4 a.u.) but one helix had twice the diameter (0.8 a.u.) of the other. As shown in FIG. 14 in the short helix 210, the catheter twisted continuously during pullback by about 110° and in the long helix by 220° (i.e., twice as much). The overlaid lines in FIG. 14 facilitates the measurements.

Figure 15:
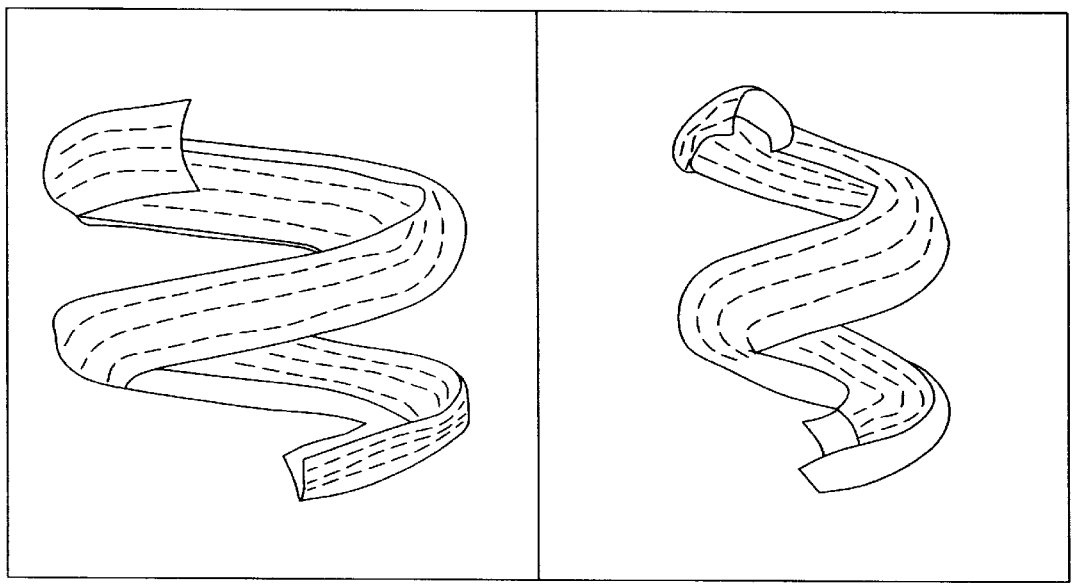
FIG. 15 is a diagram showing a shaded surface representation of the twist of the catheter during pullback.

Both helices were approximated by regular polygons of 4, 6, 8, 12, 16, 32, 48 and 64 line segments per revolution and the catheter twist was calculated using our sequential triangulation method. In FIG. 13, the triangulation-based twist is compared with the values derived by differential geometry (solid lines) for the wide helix (below) and the narrow helix (above) for the different levels of sampling accuracy. Our sequential triangulation method overestimates the analytically derived torsion by less than 3% (dotted lines) if the helices are approximated by polygons of 16 or more line segments per revolutions; the overestimation is less than 1% for polygons with 24 or more line segments. To visualize the twist of the catheter during pullback, the polygons of FIG. 13 were approximated by Bezier curves along which a half-circular cross section was swept. A shaded surface representation of the twist of the catheter during pullback is shown in FIG. 15.

The linear twist pattern predicted for helical pullbacks agreed well with the twist of the IVUS catheter actually measured in pullback images obtained in helical vessel phantoms. The amount of twist measured in the phantoms was however overestimated by the mathematical model by about 1% per cm pullback length. In general, the rate of catheter twist during pullback is determined in a nonlinear way by the ration between the displacement per revolution and the diameter of the helix. Increasing the displacement per revolution while keeping the diameter constant increases the rate of twist. The same effect results from decreasing the diameter while keeping the displacement per revolution constant. In addition, the twist of the catheter increases linearly with the length of the pullback.

The preferred embodiments were used for in-vitro imaging of pig hearts. A 9-in field of view NOV) was used for image acquisition. For registration of geometric image distortion, 8-point grids were fixed in front of both image intensifiers after being centered and adjusted vertically with a level (the grid points are visible in FIG. 6). The biplane gantry was set to the posterior-anterior/lateral projection again utilizing a level. The frontal and lateral system were adjusted to a common isocenter using a wooden calibration ball (85 mm diameter) that was required to be projected to the center of the grids at both image intensifiers. From this point on, only the source-image intensifier distance (SID) was allowed to change; for each biplane recording, the SID was measured manually with a ruler.

A tortuous coronary artery of a cadaveric pig heart was catherized and pressurized with 0.9% saline at about 100 mmHg. The pig heart was immersed into a cylindrical container (100×200 mm) filled with warm water at body temperature. The IVUS catheter was inserted into the coronary artery and advanced into position under fluoroscopic control with help of a guidewire. After removing the guidewire, diluted contrast agent was injected into the coronary artery and the pig heart was recorded for 3–5 seconds on biplane cine film. The IVUS catheter was pulled back manually at approximately constant speed of 1 mm/s. The acquired IVUS images were recorded on S-VHS videotape together with real-time clock data. The starting and stopping time of the pullback was protocolled. A second biplane angiogram was recorded on cine film showing the final position of the IVUS catheter.

The proposed method for geometrically correct 3D reconstruction of coronary arteries based on biplane angiography and IVUS pullbacks has been applied to five (two left, three right) tortuous coronary vessel segments in three cadaveric pig hearts. None of the vessels examined so far showed signed of atherosclerosis.

Figure 16:
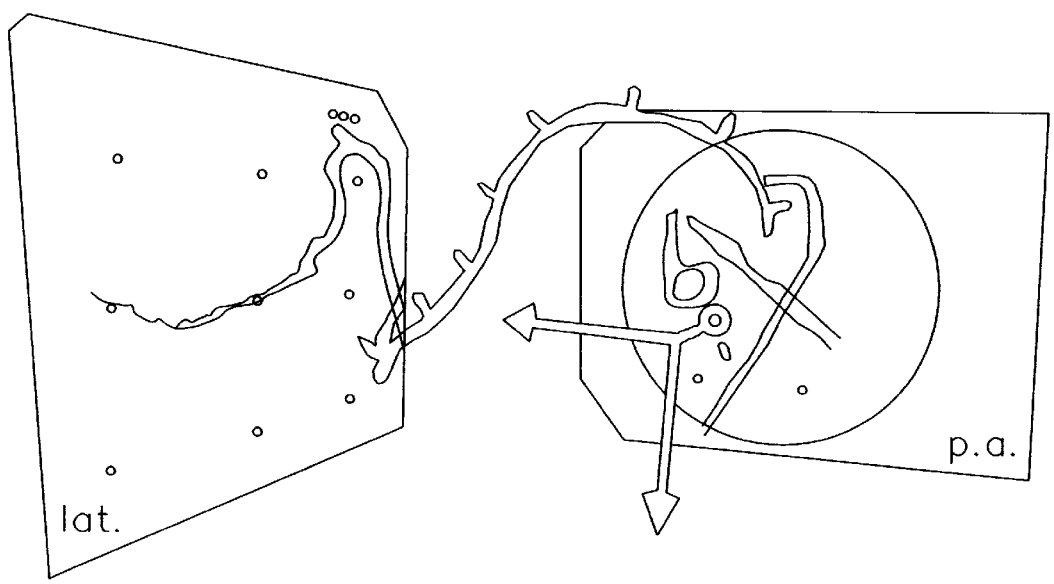
FIG. 16 is a diagram showing a perspective view of angiograms and a reconstructed catheter centerline.

One setup allowed the identification and 3D reconstruction of the IVUS catheter centerline in the biplane angiograms (lateral view shown in FIG. 6). The IVUS catheter was withdrawn over a length of 145 mm. The reconstructed length of the pullback was slightly longer (146.6 mm) presumably due to small amounts of noise remaining after polygon smoothing. A perspective view of the angiograms and the reconstructed catheter centerline is shown in FIG. 16 generated by a VRML (Virtual Reality Modeling Language) scene description of the cadaveric pig heart setup. The orientation of the IVUS images along the pullback path is indicated by short vectors as derived by our sequential triangulation method. The world coordination system has its original at the isocenter of the biplane gantry system with one unit of the axes corresponding to 10 mm in the real world.

Although the preferred embodiments of the present invention were described using a 3D representation of a tortuous heart vessel, the present invention is not intended to be so limited. Alternative combinations of information providing a 3D path and information obtained regarding the 3D path through a tortuous vessel can also be used. For example, other possible applications for the evaluation and diagnosis for human or animal treatment can include arthroscopic inspection and surgery. Further potential body vessels for inspected and diagnosed include areas of the brain, colon, sinus, etc.

Figure 17:
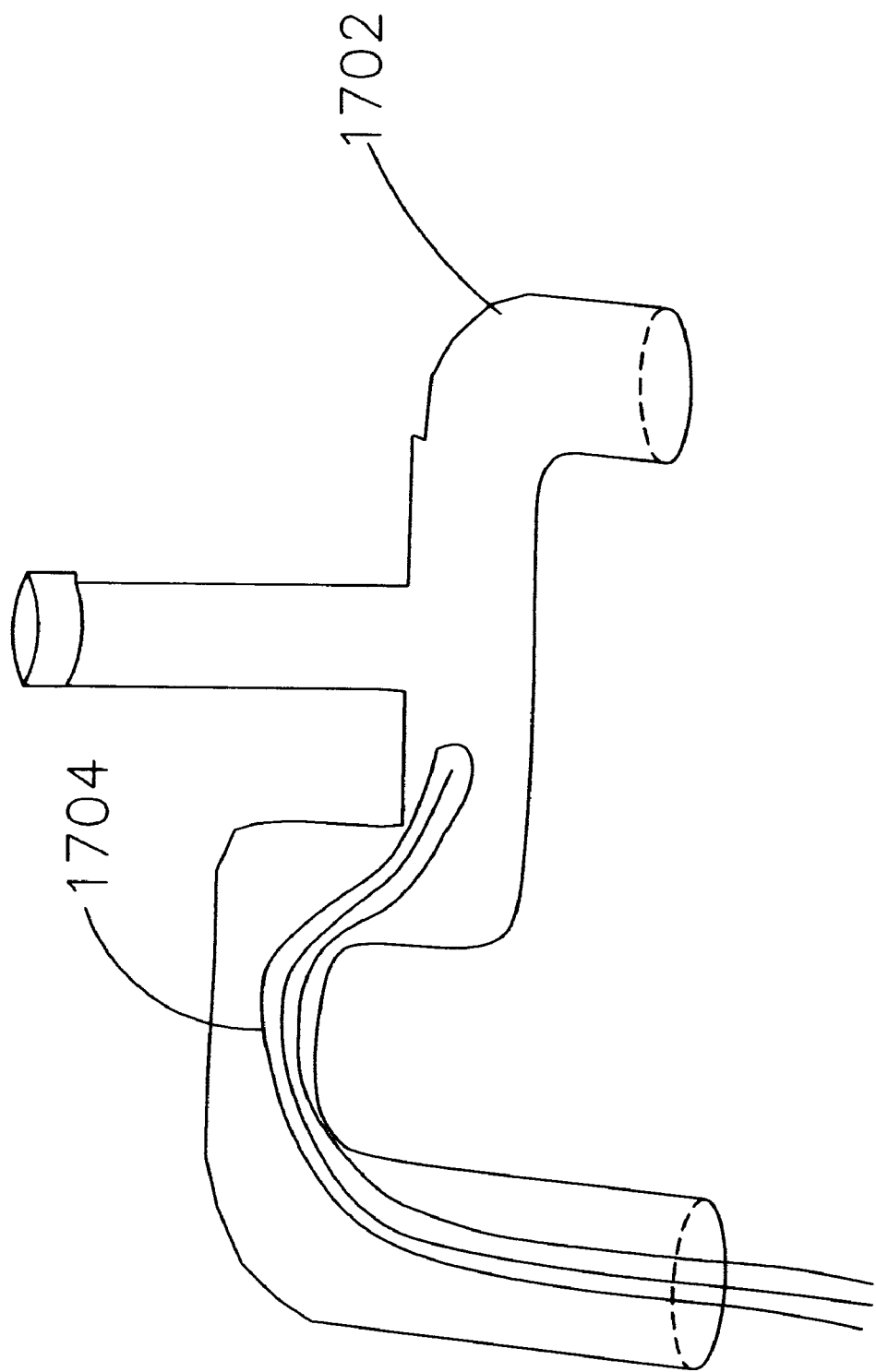
FIG. 17 is a diagram showing of a piping assembly.

In addition, industrial applications such as nuclear power plants or areas where a 3D representation of a tortuous vessel, such as a piping assembly for cooling or material supply, is known or can be represented. In this case, information regarding the interior of the piping assembly or the like requires accurate 3D representation. However, only indirect information regarding the interior of the piping assembly can be obtained. For example, indirect information can be obtained using a probe, a remotely controlled robotic object or the like inserted inside the piping assembly to retrieve information regarding the piping assembly, deposits on the piping assembly or the like. As shown in FIG. 17, a piping assembly 1702 has a predetermined 3D path. In addition, a probe 1704 having a representable internal energy can be inserted. As discussed in detail above, the 3D path of the probe (external energy) and the probe 1704 itself (internal energy) will affect data fusion between information regarding the inside of the piping assembly 1702 and its 3D path. In this case, the probe 1704 can be a fiber optic cable including a optical sensor that actively or passively generates 2D image information (e.g., deposits, corrosion, reflected light, Doppler effects or the like) regarding the interior or portions of the interior of the piping assembly over a pullback path. Alternatively, the probe could be an ultrasound sensor, a magnetic sensor or an infrared sensor for cross-sectional temperature representations and evaluation.

Three-dimensional reconstruction based on data fusion biplane angiography and IVUS pullback imaging provides useful additional information about the tortuosity of any examined coronary artery and the longitudinal twist of the IVUS catheter during pullback. Both factors strongly influence the reconstructed shape and location of a coronary lesion and thus may have an impact on the diagnostic/ therapeutic judgment.

An important advantage of our approach to catheter twist calculation is the establishment of a positional and rotational relationship between the pullback images. If single images in the pullback sequence are rotationally adjusted by anatomic landmarks (e.g., vessel bifurcations visible in both angiography and IVUS) the orientation of the remaining frames is fixed (single landmark) or may be interpolated (multiple landmarks). Thus, local knowledge about orientation of IVUS images propagates across the entire pullback.

Beneficially, the result using the preferred embodiments depends in a continuous way on the detected borders both in the angiograms and the IVUS images. Further, the geometric ambiguities inherent in angiographic projections are accounted for.

The minimally disturbing and largely automated protocol for image acquisition and subsequent processing operates well in a clinical setting. Further, luminal morphology and mural pathology are displayed simultaneously. The spatial distribution and location of plaque within atherosclerotic coronaries is reconstructed correctly. This allows for a better planning, guidance, and assessment of therapeutic interventions, as well as a better estimation of the actual flow pattern characteristics.

The foregoing embodiments are merely exemplary and are not to be construed as limiting the present invention. The present teaching can be readily applied to other types of apparatuses. The description of the present invention is intended to be illustrative, and not to limit the scope of the claims. Many alternatives, modifications, and variations will be apparent to those skilled in the art.

What is claimed is:

1. An apparatus for determining three dimensional representations of a tortuous vessel, comprising:

an external information processing unit for receiving a first set of images of a line object in the tortuous vessel, determining external energy information of said first set of images and outputting said external energy information;

an internal information processing unit for receiving internal information related to the line object including a minimum bending radius, determining internal energy information of the line object and outputting said internal energy information;

a 3D pullback path determination unit for receiving said external energy information and said internal energy information and determining a 3D pullback path that is physically feasible based on the line object; and means for receiving said 3D pullback path and for calculating three dimensional representations of the tortuous vessel based on said 3D pullback path, wherein the means for receiving and calculating receives 2D representations of the interior of the tortuous vessel at a plurality of points along the 3D pullback path, and wherein the means for receiving and calculating comprises a global interpolating means for interpolating using global behavior of the line object to approximate a local behavior between corresponding points of the plurality of 2D representations of the interior of the tortuous vessel, wherein the interpolating using the global behavior determines the three dimensional representations of the tortuous vessel.

2. The apparatus according to claim 1, wherein the external information processing unit receives the first set of images of the line object in the tortuous vessel from at least one of a biplane angiographic unit and an intravascular ultrasound imaging unit, and wherein the line object is a catheter.

3. The apparatus according to claim 1, wherein the external information processing unit determines the external energy information based on at least one of a plurality of 2D cross-sectional images of the tortuous vessel and multiple projection images with prescribed epipolar geometry of the tortuous vessel.

4. The apparatus according to claim 1, wherein the internal energy information represents physical properties of the line object.

5. The apparatus according to claim 1, wherein the internal information processing unit receives internal information including at least one of modulus of elasticity, cross-sectional shape, diameter, wall thickness, and stiffness.

6. The apparatus according to claim 1, wherein the internal information processing unit determines a 3D representation of the line object.

7. The apparatus according to claim 1, wherein the means for receiving and calculating comprises:
   a catheter twist determination unit;
   a correlation determination unit; and
   an interpolation unit that uses Bezier curves to determine the three dimensional representations of the tortuous vessel between specifically determined positions, wherein the interpolation unit is the global interpolating means.

8. The apparatus according to claim 1, wherein the means for receiving and calculating comprises a calculation unit that determines with adjustable accuracy the three dimensional representations of the tortuous vessel between specific positions.

9. A method for determining three dimensional representations of a tortuous vessel, comprising:
   determining external information of the tortuous vessel;
   determining internal information of a line object sensor;
   determining a 3D pullback path of the line object sensor based on the external information and the internal information; and
   calculating three dimensional representations of the tortuous vessel based on the 3D pullback path, wherein the calculating step comprises,
      receiving a plurality of 2D cross-sectional images of the interior of the tortuous vessel, and
      interpolating using global behavior of the line object sensor,
   wherein a local behavior between corresponding points of the plurality of 2D cross-sectional images is represented by an approximation utilizing behavior of the entire line object sensor to determine the three dimensional representations of the tortuous vessel between the corresponding points of the plurality of 2D cross-sectional images, and wherein the determining a 3D pullback path of the line object sensor step comprises,
      constructing a 3D cost volume based on the external information of the tortuous vessel,
      constructing a 3D representation of the line object sensor based on the internal information of the line object sensor including at least a minimum bending radius,
      determining a low cost path of the line object sensor through the 3D cost volume that is physically feasible for the line object sensor, and
      interpolating the physically feasible low cost path using the global behavior of the line object sensor.

10. The method of claim 9, wherein the corresponding points of the plurality of 2D cross-sectional images are border points of lumen in adjacent ones of the plurality of 2D cross-sectional images.

11. The method of claim 9, wherein the determining external information step comprises:
   receiving a plurality of 2D representations of cross-sectional information along the 3D pullback path; and
   receiving at least one set of multiple 2D projection images with prescribed epipolar geometry of the tortuous vessel, wherein the 2D representations of cross-sectional information are obtained using an intravascular ultrasound imaging unit, wherein the at least one set of multiple 2D projection images with prescribed epipolar geometry are initial and final images of the line object sensor in the tortuous vessel obtained using a biplane angiographic unit.

12. The method of claim 9, wherein the determining external information step comprises:
   receiving a plurality of 2D representations of cross-sectional information along the 3D pullback path; and
   receiving at least one set of multiple 2D projection images with prescribed epipolar geometry of the tortuous vessel, wherein the at least one set of multiple 2D projection images with prescribed epipolar geometry includes an initial position of the line object sensor in the tortuous vessel, and wherein the 2D cross-sectional images include at least one of lumen, plaque, wall and adventitia.

13. The method of claim 9, wherein the determining a 3D pullback path of the line object sensor step comprises:
   determining 3D volume representation of the external information; and
   determining optimal location of a representation of the line object sensor in the 3D volume representation.

14. The method of claim 9, further comprising:
   determining a 3D volume representation of the external information; and
   determining a low energy location of a 3D representation of the line object sensor in the 3D volume representation;
   determining total internal energy of the line object sensor in the low energy location;
   comparing the total internal energy of the line object sensor to a threshold; and
   modifying the 3D volume representation and repeating the determining a low energy location through comparing the total internal energy steps when the total internal energy level is greater than the threshold.

15. The method of claim 9, wherein the calculating three dimensional representations of the tortuous vessel step comprises:
   determining a centerline of the plurality of 2D cross-sectional images of the interior of the tortuous vessel; and
   using a global smoothing process to perform local smoothing of the three dimensional representations of the tortuous vessel between points mapped to the 2D centerline.

16. The method of claim 9, wherein the global smoothing characteristics include variable levels of interpolation based on Bezier curves.

* * * * *